US012709598B2

(12) United States Patent
Zhang et al.

(10) Patent No.: US 12,709,598 B2
(45) Date of Patent: Aug. 18, 2026

(54) SYNTHESIS OF 6-ARYL-4-AMINOPICOLINATES

(71) Applicant: CORTEVA AGRISCIENCE LLC, Indianapolis, IN (US)

(72) Inventors: Chunming Zhang, Zionsville, IN (US); Siyu Tu, Midland, MI (US); Ronald B. Leng, Midland, MI (US); Nicholas Irvine, Westfield, IN (US); Abraham Schuitman, Zionsville, IN (US); Aaron Shinkle, Brownsburg, IN (US); Jayachandran Devaraj, Zionsville, IN (US); Chengli Zu, Carmel, IN (US)

(73) Assignee: CORTEVA AGRISCIENCE LLC, IN (US)

( * ) Notice: Subject to any disclaimer, the term of this patent is extended or adjusted under 35 U.S.C. 154(b) by 867 days.

(21) Appl. No.: 17/906,404

(22) PCT Filed: Mar. 17, 2021

(86) PCT No.: PCT/US2021/022738

§ 371 (c)(1),
(2) Date: Sep. 15, 2022

(87) PCT Pub. No.: WO2021/188654

PCT Pub. Date: Sep. 23, 2021

(65) Prior Publication Data

US 2023/0174490 A1 Jun. 8, 2023

Related U.S. Application Data

(60) Provisional application No. 62/991,284, filed on Mar. 18, 2020.

(51) Int. Cl.
*C07D 213/803* (2006.01)
*C07D 401/04* (2006.01)
*B01J 23/44* (2006.01)

(52) U.S. Cl.
CPC ....... *C07D 213/803* (2013.01); *C07D 401/04* (2013.01); *B01J 23/44* (2013.01)

(58) Field of Classification Search
CPC ..... C07D 213/803; C07D 401/04; B01J 23/44
USPC ....................................................... 546/277.1
See application file for complete search history.

(56) References Cited

U.S. PATENT DOCUMENTS

| | | | | |
|---|---|---|---|---|
| 6,784,137 | B2 * | 8/2004 | Balko | C07D 409/04 546/268.1 |
| 8,871,943 | B2 | 10/2014 | Renga et al. | |
| 9,067,890 | B2 | 6/2015 | Arndt et al. | |
| 9,452,984 | B2 | 9/2016 | Arndt et al. | |
| 10,087,164 | B2 * | 10/2018 | Fisk | C07D 213/79 |
| 11,401,242 | B2 | 8/2022 | Devaraj et al. | |
| 2012/0190548 | A1 * | 7/2012 | Eckelbarger | A01N 55/00 546/310 |
| 2012/0190549 | A1 * | 7/2012 | Eckelbarger | C07F 7/0812 546/14 |
| 2012/0190857 | A1 * | 7/2012 | Arndt | C07D 213/803 546/310 |
| 2014/0274695 | A1 | 9/2014 | Eckelbarger et al. | |
| 2017/0334878 | A1 * | 11/2017 | Fisk | B01J 31/00 |
| 2023/0167061 | A1 | 6/2023 | Hazari et al. | |
| 2023/0357155 | A1 | 11/2023 | Canturk et al. | |

FOREIGN PATENT DOCUMENTS

| | | | |
|---|---|---|---|
| DE | 102016122812 | A1 | 5/2018 |
| WO | 2011146287 | A1 | 11/2011 |
| WO | 2012103041 | A2 | 8/2012 |
| WO | 2012103047 | A1 | 8/2012 |
| WO | 2014018502 | A1 | 1/2014 |
| WO | 2014151005 | A1 | 9/2014 |
| WO | 2018208582 | A1 | 11/2018 |

OTHER PUBLICATIONS

Miyaura & Suzuki, Chem. Rev. 1995, 95, 2457-2483 (Year: 1995).*
International Search Report and Written Opinion for International Application No. PCT/US21/22738, mailed May 11, 2021.
Whiteker Gregory T. et al: "Synthesis of 6-Aryl-5-fluoropicolinate Herbicides via Halex Reaction of Tetrachloropicolinonitrile", Organic Process Research & Development, [Online] vol. 23, No. 10, Oct. 18, 2019 (Oct. 18, 2019), pp. 2166-2174, XP055799559, US ISSN: 1083-6160, DOI: 10.1021/acs.oprd.9b00197; Retrieved from the Internet: URL:https://pubs.acs.org/doi/pdf/10.1021/acs.oprd.9b00197> [retrieved on Oct. 18, 2019] scheme 2; compounds 4,6.
Epp Jeffrey B. et al: "The discovery of Arylex(TM) active and Rinskor(TM) active: Two novel auxin herbicides", Bioorganic & Medicinal Chemistry, vol. 24, No. 3, Feb. 1, 2016 (Feb. 1, 2016), pp. 362-371, XP055782687, Amsterdam, NL; ISSN: 0968-0896, DOI: 10.1016/j.bmc.2015.08.011 scheme 2, compounds 20-22, 25.
Canturk Belgin et al: "Identification and Synthesis of a Nitrophenyl Metabolite of Rinskor Active from Terrestrial Aerobic Soil Studies", Organic Process Research & Development, vol. 23, No. 10, Oct. 18, 2019 (Oct. 18, 2019), pp. 2234-2242, XP055799552, US ISSN: 1083-6160, DOI: 10.1021/acs.oprd.9b00290; Retrieved from the Internet: URL:https://pubs.acs.org/doi/pdf/10.1021/acs.oprd.9b00290> scheme 1, 18.
International Preliminary Report on Patentability for International Application No. PCT/US2021/022738, mailed Sep. 29, 2022, 8 Pages.
Abdel-Hafez A.A-M., "Synthesis and Anticonvulsant Evaluation of N-Substituted-Isoindolinedione Derivatives," Archives of Pharmacal Research, Published by Springer Science—Business Media, Korea, 2004, vol. 27, No. 5, pp. 495-501.
International Preliminary Report on Patentability for International Application No. PCT/US2021/022716, mailed Sep. 29, 2022, 7 pages.

(Continued)

*Primary Examiner* — Andrew D Kosar

(57) ABSTRACT

The present disclosure relates to improved methods of synthesizing 6-aryl-4-aminopicolinates, such as arylalkyl and alkyl 4-amino-3-chloro-6-(4-chloro-2-fluoro-3-methoxyphenyl)pyridine-2-carboxylates.

1 Claim, No Drawings

(56) References Cited

OTHER PUBLICATIONS

International Search Report and Written Opinion for International Application No. PCT/US2021/022716, mailed May 11, 2021, 10 pages.
Joshi S., et al., "A Facile Synthesis and Antimicrobial Activity of Different Phthalimides Having Heterocyclic Moiety," Indian Journal of Heterocyclic Chemistry, Published by Connect Journals, India, Oct.-Dec. 2018, vol. 28, No. 4, pp. 459-465.
Sakthivel K., et al., "Direct SNAr Amination of Fluorinated Imidazo[4,5-c]-Pyridine Nucleosides: Efficient Syntheses of 3-Fluoro-3-Deazaadenosine Analogs," Tetrahedron Letters, Elsevier, 2005, vol. 46, No. 22, pp. 3883-3887.

* cited by examiner

SYNTHESIS OF 6-ARYL-4-AMINOPICOLINATES

CROSS-REFERENCE TO RELATED APPLICATIONS

This application claims priority to International (PCT) Patent Application Serial No. PCT/US21/22738, filed Mar. 17, 2021, and entitled "IMPROVED SYNTHESIS OF 4-AMINO-6-(HETEROCYCLIC) PICOLINATES," which claims priority to U.S. Provisional Application Ser. No. 62/991,284, filed on Mar. 18, 2020, the entire disclosure of which is hereby expressly incorporated by reference.

FIELD

The present disclosure concerns improved processes for the preparation of 6-aryl-4-aminopicolinates. More particularly, the present disclosure concerns an improved process for the preparation of 6-aryl-4-aminopicolinates from 6-bromo-4-aminopicolinates.

BACKGROUND

6-Aryl-4-aminopicolinates, such as arylalkyl and alkyl 4-amino-3-chloro-5-fluoro-6-(4-chloro-2-fluoro-3-methoxyphenyl)picolinates, are high value herbicides recently developed and marketed by Dow AgroSciences LLC. U.S. Patent Application Publication 20120190857 A1 and U.S. Pat. Nos. 7,314,849 B2, 8,609,853 B2, 8,609,855 B2, 8,754,231 B2, 8,836,688 B2, 10,087,164 B2, 10,544,121 B2, and 10,570,114 B2 (the disclosure of each is explicitly incorporated by reference herein) describe inter alia certain 6-aryl-4-aminopicolinates and syntheses thereof. The syntheses for these 6-aryl-4-aminopicolinates involve reacting a 6-chloropicolinic acid or 6-chloropicolinate head with an aryl boronic acid or aryl boronate tail. The reaction scheme for 6-aryl-4-aminopicolinates is shown in Scheme 1.

Scheme 1

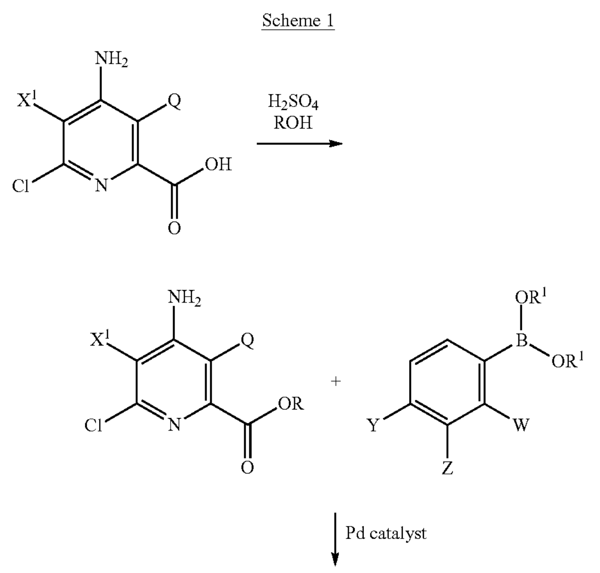

-continued

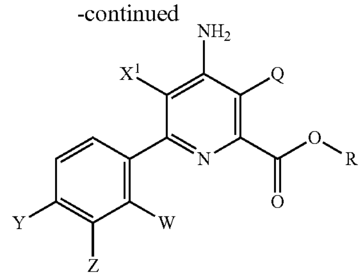

Q = H or Cl; R = alkyl or arylalkyl; $R^1$ = H, alkyl, or branched alkyl; W = H, F, alkyl, or alkoxy; $X^1$ = H, F, or Cl; Y = Cl; and Z = alkoxy It would be useful to have a higher yielding process route to these 6-aryl-4-aminopicolinate compounds.

SUMMARY

The present disclosure concerns an improved process for the preparation of 6-aryl-4-aminopicolinates of Formula I.

In some embodiments, the disclosure concerns a process for the preparation of 6-aryl-4-aminopicolinates of Formula I Formula I

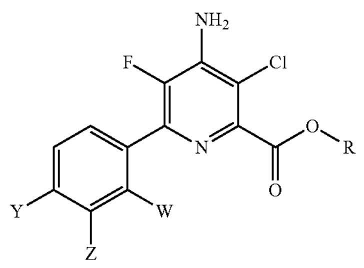

wherein

R represents H, $C_1$-$C_{12}$ alkyl, $C_3$-$C_{12}$ alkynyl, $C_1$-$C_3$ alkyl substituted with CN, or $C_6$-$C_{12}$ arylalkyl;

W represents H, halogen, $C_1$-$C_4$ alkyl, or $C_1$-$C_3$ alkoxy;

Y represents halogen, $C_1$-$C_4$ alkyl, $C_1$-$C_4$ haloalkyl, $C_1$-$C_4$ alkoxy, $C_1$-$C_4$ haloalkoxy, —CN, or —$NO_2$; and Z represents H, F, Cl, $C_1$-$C_4$ alkyl, $C_1$-$C_3$ alkoxy, $C_1$-$C_4$ haloalkyl, $C_1$-$C_3$ haloalkoxy, $C_1$-$C_4$ alkoxy-substituted $C_1$-$C_4$ alkyl, or —$NR^2R^3$, wherein $R^2$ and $R^3$ are independently hydrogen, $C_1$-$C_3$ alkyl or $C_1$-$C_3$ haloalkyl;

the process comprising the following steps:

a) creating a first mixture containing a compound of Formula A,

Formula A

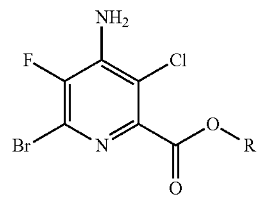

wherein

R represents H, $C_1$-$C_{12}$ alkyl, $C_3$-$C_{12}$ alkynyl, $C_1$-$C_3$ alkyl substituted with CN, or $C_6$-$C_{12}$ arylalkyl;

a compound of Formula B,

Formula B

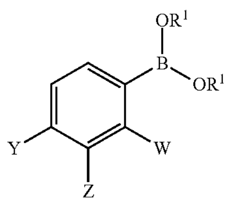

wherein

- $R^1$ represents H, $C_1$-$C_6$ alkyl, or alternatively two $R^1$ may form a $C_2$-$C_6$ alkyl linkage, which together with B and two 0 form a 5- to 9-atom cyclic structure;
- W represents H, halogen, $C_1$-$C_4$ alkyl, or $C_1$-$C_3$ alkoxy;
- Y represents halogen, $C_1$-$C_4$ alkyl, $C_1$-$C_4$ haloalkyl, $C_1$-$C_4$ alkoxy, $C_1$-$C_4$ haloalkoxy, —CN, or —$NO_2$; and
- Z represents H, F, Cl, $C_1$-$C_4$ alkyl, $C_1$-$C_3$ alkoxy, $C_1$-$C_4$ haloalkyl, $C_1$-$C_3$ haloalkoxy, $C_1$-$C_4$ alkoxy-substituted $C_1$-$C_4$ alkyl, or —$NR^2R^3$, wherein $R^2$ and $R^3$ are independently hydrogen, $C_1$-$C_3$ alkyl or $C_1$-$C_3$ haloalkyl;

one or more bases; and one or more solvents;

b) adding a palladium catalyst, and optionally a ligand to the first mixture to form a second mixture; and c) heating the second mixture to a temperature of between about 25° C. and about 100° C.

The components of each mixture listed in the steps above such as Formula A, Formula B, the one or more bases, and the one or more solvents used to form the first mixture may be combined in a different order than specified. The order in which the components are added to form the mixtures in the present disclosure is not limited to the order illustrated.

DETAILED DESCRIPTION

As used herein, the term "alkyl" refers to saturated hydrocarbon moieties that are straight-chained or branched. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples of alkyl groups include, but are not limited to, methyl, ethyl, propyl, butyl, isopropyl, isobutyl, tertiary butyl, pentyl, and hexyl. As used herein, the term "cycloalkyl" refers to saturated hydrocarbon moieties that are cyclic. Examples of cycloalkyl groups include, but are not limited to, cyclopropyl, cyclobutyl, cyclopentyl, cyclohexyl, and the like. Alkyl and cycloalkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the terms "haloalkyl" and "halocycloalkyl" refer to alkyl and cycloalkyl groups, respectively, as defined above, wherein these groups the hydrogen atoms may be partially or entirely substituted with halogen atoms. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples include, but are not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, and 1,1,1-trifluoroprop-2-yl. Haloalkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "alkynyl" represents straight-chained or branched hydrocarbon moieties containing a triple bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkynyl groups are intended. Alkynyl groups may contain more than one unsaturated bond. Examples include, but are not limited to, $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "aryl," as well as derivative terms such as aryloxy, refers to groups that include a monovalent aromatic carbocyclic group of from 6 to 14 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more chemical moieties. Examples of suitable substituents include, for example, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl and $C_1$-$C_2$ haloalkyl.

As used herein, the term "arylalkyl" refers to an alkyl group substituted with an unsubstituted or substituted aryl group. $C_7$-$C_{10}$ arylalkyl refers to a group wherein the total number of carbon atoms in the group is 7 to 10, not including the carbon atoms present in any substituents of the aryl group.

As used herein, alkoxy refers to a group of the formula R—O—, where R is alkyl as defined above. Unless otherwise specified, alkoxy groups wherein R is a $C_1$-$C_8$ alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, haloalkoxy refers to a group of the formula R—O—, where R is haloalkyl as defined above. Unless otherwise specified, haloalkoxy groups wherein R is a $C_1$-$C_8$ alkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro,2-difluoroethoxy, 2,2-dichloro-2-fluoroethoxy, 2,2,2-trichloroethoxy, pentafluoroethoxy, and 1,1,1-trifluoroprop-2-oxy.

The terms "isolate," "isolating," or "isolation" as used herein mean to partially or completely remove or separate the desired product from the other components of a finished chemical process mixture using standard methods such as, but not limited to, filtration, extraction, distillation, crystallization, centrifugation, trituration, liquid-liquid phase separation or other methods known to those of ordinary skill in the art. The isolated product may have a purity that ranges from <50% to >50%, and may be purified to a higher purity level using standard purification methods. The isolated product may also be used in a subsequent process step with or without purification.

The term "palladium catalyst" used herein means a molecule or compound generated from a palladium compound and a ligand or a preformed compound containing palladium and a ligand. Examples of palladium compounds include, but are not limited to, palladium(II) acetate ($Pd(OAc)_2$) and palladium(II) chloride ($PdCl_2$). Examples of ligands include, but are not limited to, tri-tert-butylphosphine, tricyclohexylphosphine, di-tert-butylphenylphosphine, dicyclohexylphenylphosphine, triphenylphosphine, tri(o-tolyl)phosphine, 1,2-bis(diphenylphosphino)ethane, 1,3-bis(diphenylphosphaneyl)propane, 1,4-bis(diphenylphosphino)butane, 1,1'-ferrocenediyl-bis(diphenylphosphine) (dppf). Examples of a preformed compound containing palladium and a ligand include, but are not limited to, bis(triphenylphosphine)palladium(II) dichloride, bis(acetato)bis(triphenylphosphine)palladium(II), tetrakis(triphenylphosphine)palladium(0), and tris(dibenzylideneacetone)dipalladium(0).

Flurorinating compound or fluorinating mixture of compounds as used herein means a compound capable of installing a fluorine atom on a compound. Examples of fluorinating compounds or fluorinating mixtures of compounds include, but are not limited to, is potassium fluoride, cesium fluoride, tetramethylammonium fluoride, potassium fluoride/tetramethylammonium chloride, cesium fluoride/tetramethylammonium chloride, tetramethylammonium fluoride/tetramethylammonium chloride, or mixtures thereof.

"Acylation catalyst" as used herein means a compound that accelerates the reaction that adds an acyl group (i.e., —C(O)— group to another compound. Examples of acylation catalysts include, but are not limited to, 4-(dimethylamino)pyridine (DMAP) and N-methylimidazole.

"Continuous flow", "flow", "continuous formation", "continuous process", or other derivative terms as used herein means methods that produce a minimum amount of a reactive intermediate at any given time and provide reduced cycle times in comparison to conventional methods. U.S. Pat. No. 9,145,428 B2 (the disclosure of which is explicitly incorporated by reference herein) describes methods and systems using continuous flow.

In the processes described herein the 6-aryl-4-aminopicolinates of Formula I, wherein R, W, Y, and Z are as previously defined, may be prepared by reacting of compound of Formula A, wherein R is as previously defined, with a compound of Formula B, wherein $R^1$, W, Y, and Z are as previously defined. U.S. Pat. Nos. 7,314,849 B2 and 7,611,647 B2 (the disclosure of each is explicitly incorporated by reference herein) describe inter alia the synthesis of compounds of Formula B. Compounds of Formula A may be prepared from 4-amino-3,5,6-trichloropicolinic acid (Picloram), or esters or derivatives thereof.

Formula I

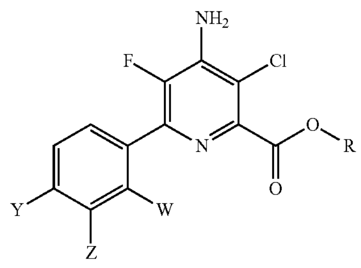

A process for the preparation of compounds of Formula A is depicted in Scheme 2. In one embodiment, 3,5,6-trichloropicolinic acid (Picloram, C2) may be converted to the corresponding ester D2, wherein $Z^1$ is COOR and R is not H, via methods that include, but are not limited to, coupling the acid C2 with an alcohol ROH, wherein R is $C_1$-$C_{12}$ alkyl, $C_3$-$C_{12}$ alkynyl, $C_1$-$C_3$ alkyl substituted with CN, or $C_6$-$C_{12}$ arylalkyl, using any number of suitable activating agents such as those used for peptide couplings including dicyclohexylcarbodiimide (DCC), N-(3-dimethylaminopropyl)-N'-ethylcarbodiimide hydrochloride (EDCI), or carbonyl diimidazole (CDI); forming the acid chloride of C2 by reaction with thionyl chloride or oxalyl chloride in the presence of an alcohol ROH, wherein R is as previously defined; contacting the acid C2 with an alcohol ROH, wherein R is as previously defined, in the presence of an acid; and reacting the compound of Formula C2 with alkylating agents such as substituted or unsubstituted alkyl halides, substituted or unsubstituted arylalkyl halides, or substituted or unsubstituted alkyl sulfonates in the presence of one or more bases such as triethylamine, N,N-diisopropylethylamine, 3,5-lutidine, 2,6-lutidine, 3-methylpyridine, or lithium or potassium carbonate, in a solvent such as tetrahydrofuran, dimethyl sulfoxide, N,N-dimethylformamide, dichloromethane, or 1,2-dichloroethane as in step a of Scheme 2.

The ester D2 ($Z^1$ is COOR, R is not H) or nitrile C1 ($Z^1$ is CN) may be transformed to the corresponding phthalimides, E1 and E2, respectively, wherein A represents the substitution on the phthalimide and is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, and nitro, wherein n is 1, 2, 3, or 4; and $Z^1$ is as previously defined; by reaction with a phthaloyl halide, such as phthaloyl chloride, or phthalic anhydride; optionally a base; optionally an acylation catalyst; a solvent or solvent mixture; at a temperature from ambient temperature to about 100° C. as in step b of Scheme 2. Suitable optional bases include, but are not limited to, trimethylamine, triethylamine, tripropylamine, pyridine, 2-picoline, and 3-picoline. Suitable optional acylation catalysts include, but are not limited to, 4-(dimethylamino) pyridine (DMAP) and N-methylimidazole. Suitable solvents include, but are not limited to, acetonitrile, toluene, N,N-dimethylformamide (DMF), propionitrile, benzonitrile, tetrahydrofuran (THF), 2-methyl-THF, dioxane, cyclopentyl methyl ether (CPME), monoethyleneglycol ethers, diethyleneglycol ethers, monopropyleneglycol ethers or dipropyleneglycol ethers, and methyl isobutyl ketone (MIBK), and mixtures thereof. The temperature range for conducting this step may range from about 25° C. to about 100° C., from about 25° C. to about 90° C., from about 25° C. to about 80° C., from about 25° C. to about 70° C., from about 25° C. to about 60° C., or from about 25° C. to about 55° C., and the reaction may be conducted over a time period ranging from about 1 hour to about 72 hours, from about 1 hour to about 48 hours, from about 1 hour to about 24 hours, from about 1 hour to about 12 hours, from about 1 hour to about 6 hours, from about 2 hours to about 24 hours, from about 4 hours to about 24 hours, from about 2 hours to about 12 hours, or from about 4 hours to about 12 hours.

Phthalimides E1 and E2, wherein A, n, and $Z^1$ are as previously defined, can be converted to the difluorinated compounds F1 and F2 by treatment with a fluorinating compound or a fluorinating mixture of compounds in the presence of a solvent as shown in step c of Scheme 2. Suitable fluorinating compounds or fluorinating mixture of compounds include, but are not limited to, potassium fluoride (KF), cesium fluoride (CsF), and tetramethylammonium fluoride (TMAF), and mixtures thereof, or a mixture of tetramethylammonium chloride (TMAC) with KF or CsF. Suitable solvents include, but are not limited to, polar aprotic solvents such as acetonitrile, propionitrile, benzonitrile, dimethylsulfoxide (DMSO), N,N'-dimethylformamide (DMF), sulfolane, N,N-dimethylacetamide (DMA), 1,1-dimethyl-2-imidazolidinone (DMI), N,N'-dimethylpropyieneurea (DMPU), N-methylpyrrolidinone (NMP), tetrahydrofuran (THF), 2-methyltetrahydrofuran (2-methyl-THF), dioxane, monoethyleneglycol ethers, diethyleneglycol ethers, monopropyleneglycol ethers, or dipropyleneglycol ethers, and mixtures thereof. It is generally preferred to conduct this reaction under anhydrous or near-anhydrous conditions. These anhydrous or near-anhydrous conditions may be obtained by prior drying of the reactants and solvents. One way to dry the reactants and/or solvents is by removal by distillation of a portion of the solvent prior to conducting the reaction. Suitable reaction temperatures may be a temperature of at least about 0° C., at least about 10° C., at least about 20° C., at least about 25° C., at least about 30° C., at least about 40° C., at least about 50° C., at least about 60° C., at least about 70° C., at least about 80° C., at least about 90° C., or at least about 100° C. The reaction may be conducted at a temperature of about 0° C. to about 50° C., from about 10° C. to about 50° C., from about 25° C. to about 50° C., from about 15° C. to about 150° C., from about 25° C. to about 150° C., from about 35° C. to about 125° C., from about 45° C. to about 115° C., from about 55° C. to about 110° C., from about 65° C. to about 110° C., from about 75° C. to about 110° C., from about 85° C. to about 110° C., from about 90° C. to about 110° C., from about 50° C. to about 100° C., from about 60° C. to about 100° C., from about 70° C. to about 100° C., from about 25° C. to about 90° C., from about 25° C. to about 80° C., about 25° C. and about 110° C., from about 25° C. to about 70° C., or from about 25° C. to about 60° C. The difluorinated compounds F1 and F2 may be isolated by employing standard isolation and purification techniques.

Compounds F1 and F2, wherein A, n, and $Z^1$ are as previously defined, may be transformed to the 4-amino-6-bromopicolinic acid of Formula A1, by treatment with hydrogen bromide or hydrobromic acid (HBr) and water, as in step d of Scheme 2. The conversion involves halogen exchange of the 6-fluoro substituent by the hydrobromic acid to provide a 6-bromo substituent, hydrolysis of the $Z^1$ substituent to a carboxylic acid, and removal of the cyclic imide group by hydrolysis to regenerate the 4-amino substituent. A co-solvent of acetic acid (HOAc) is useful to help facilitate this conversion. The HBr salt of Formula A1 may also form in this reaction. This step may be conducted in two stages, wherein the first step is conducted at lower temperature and/or with no or limited amounts of water to achieve halogen exchange of the 6-fluoro substituent, and the second stage is conducted at higher temperature and/or with more water to achieve hydrolysis of the cyclic imide group and the ester (or cyano substituent). Suitable amounts of water relative to compounds F1 and F2 on a molar basis may range from about 1 to about 30, from about 1 to about 20, from about 1 to about 10, from about 1 to about 8, from about 1 to about 6, from about 1 to about 4, from about 2 to about 5, from about 2 to about 4, or from about 3 to about 4 molar equivalents of water per mole of compounds of Formula F1 and F2. Suitable amounts of hydrobromic acid (HBr) in this step relative to the compounds of Formula F1 and F2 on a molar basis may range from about 50 to about 1, from about 40 to about 1, from about 30 to about 1, from about 20 to about 1, from about 10 to about 1, from about 8 to about 1, from about 6 to about 1, from about 3 to about 1, from about 2 to about 1, or from about 3 to about 2 molar equivalents of HBr per mole of compounds of Formula F1 and F2. The reaction may be conducted at a temperature from about 50° C. to about 150° C., from about 60° C. to about 140° C., from about 70° C. to about 130° C., from about 80° C. to about 120° C., from about 90° C. to about 120° C., or from about 100° C. to about 120° C. Formula A1 may be isolated by employing standard isolation and purification techniques, which may include, but are not limited to, separating possible by-products via solvent extraction with an organic, an aqueous, or an organic-aqueous solvent, or differential aqueous solubility at certain pH levels or ranges. The HBr salt of Formula A1 may be formed in small amounts and be present in the isolated product of Formula A1. This salt may be reduced or removed from Formula A1 by solvent extractions with water or with alcohol-water mixtures such as methanol-water. The compound of Formula A1 may be converted into the ester of Formula A, wherein R is $C_1$-$C_{12}$ alkyl, $C_6$-$C_{12}$ arylalkyl, $C_3$-$C_{12}$ alkynyl or $C_1$-$C_3$ alkyl substituted with CN, via methods that include, but are not limited to, coupling the compound of Formula A1 with an alcohol ROH, wherein R is as previously defined, using any number of suitable activating agents such as those used for peptide couplings including dicyclohexylcarbodiimide (DCC), N-(3-dimethylaminopropyl)-N'-ethylcarbodiimide hydrochloride (EDCI), or carbonyl diimidazole (CDI); contacting the compound of Formula A1 with an alcohol ROH, wherein R is as previously defined, in the presence of an acid; and reacting the compound of Formula A1 with alkylating agents such as substituted or unsubstituted alkyl halides, substituted or unsubstituted alkynyl halides, substituted or unsubstituted arylalkyl halides, or substituted or unsubstituted alkyl sulfonates in the presence of one or more bases such as triethylamine, N,N-diisopropylethylamine, 3,5-lutidine, 2,6-lutidine, 3-methylpyridine, or lithium or potassium carbonate, in a solvent such as tetrahydrofuran, dimethyl sulfoxide, N,N-dimethylformamide, dichloromethane, or 1,2-dichloroethane as in step e of Scheme 2.

In one embodiment, the compound of Formula A may be isolated by employing standard isolation and purification techniques. For example, the reaction mixture product may be isolated using standard methods as known in the art and as described herein and purified by crystallization or recrystallization using a single solvent or a mixture of two or more solvents. The reaction mixture product may be purified by washing it with or stirring it in a one-, two- or three-component solvent mixture. In one embodiment, the reaction mixture product may be purified by stirring it in an aqueous alcohol solvent mixture which can also be described as an aqueous alcohol slurry treatment. The reaction mixture product of Formula A may also be purified by dissolving it in one solvent to form a solution and then adding a second solvent to the solution to cause the compound of Formula A to crystallize out of the mixture of the two solvents.

In one embodiment, the compound of Formula A may be further treated with another solvent and base without isolation.

Scheme 2

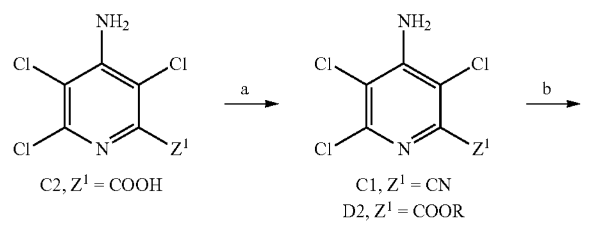

C2, $Z^1$ = COOH

C1, $Z^1$ = CN
D2, $Z^1$ = COOR

-continued

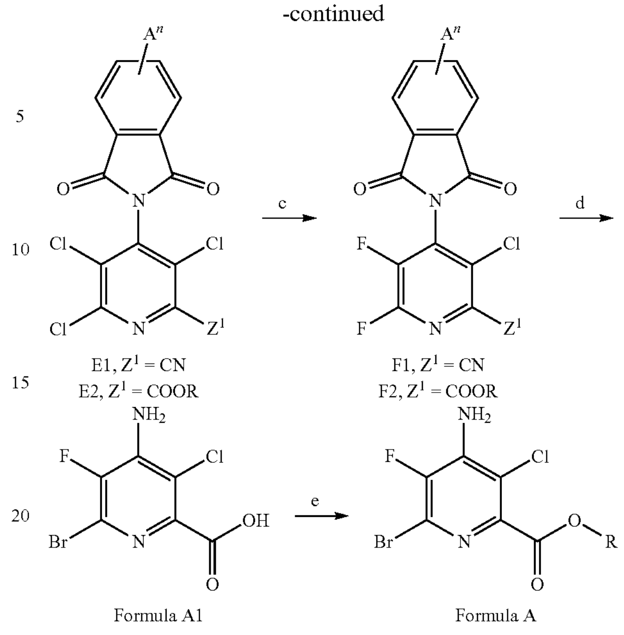

E1, $Z^1$ = CN
E2, $Z^1$ = COOR

F1, $Z^1$ = CN
F2, $Z^1$ = COOR

Formula A1

Formula A

In one embodiment, compounds of Formula I may be prepared by reaction of the compound of Formula A with a compound of Formula B, along with one or more bases, one or more solvents, a palladium catalyst and optionally, a ligand. The reaction may be deoxygenated prior to addition of the palladium catalyst and optional ligand. The reaction can be conducted at temperatures from about 25° C. to about 100° C. Suitable bases for this reaction include, but are not limited to, potassium carbonate, potassium bicarbonate, sodium carbonate, sodium bicarbonate, potassium acetate, sodium acetate, potassium phosphate monobasic, potassium phosphate dibasic, potassium phosphate tribasic, sodium tetraborate, potassium hydroxide, sodium hydroxide, cesium fluoride, potassium fluoride, triethylamine, triisopropylamine, diisopropylamine, diethylamine, and diisopropylethylamine. Preferred bases include potassium carbonate and potassium bicarbonate. Suitable solvents include, but are not limited to, methyl isobutyl ketone (MIBK), dimethoxyethane (DME), acetonitrile (MeCN), tetrahydrofuran (THF), methanol (MeOH), benzyl alcohol, toluene, water, and mixtures thereof. Suitable ligands for the palladium catalyst include, but are not limited to, bis(phosphine) ligands, trialkylphosphines and triarylphosphines. These include, but are not limited to, tri-tert-butylphosphine, tricyclohexylphosphine, di-tert-butylphenylphosphine, dicyclohexylphenylphosphine, triphenylphosphine, tri(o-tolyl)phosphine, 1,2-bis(diphenylphosphino)ethane, 1,3-bis (diphenylphosphaneyl)propane, 1,4-bis(diphenylphosphino) butane, 1,1'-ferrocenediyl-bis(diphenylphosphine) (dppf), 4-diphenylphosphinomethyl polystyrene resin crosslinked, sodium diphenylphosphinobenzene-3-sulfonate with 2% DVB, tri(p-tolyl)phosphine, and (±)-2,2'-bis(diphenylphosphino)-1,1'-binaphthyl. The concentration of the ligand can vary. In some embodiments, the concentration of the ligand is from about 0.4% to about 8.0% relative to the limiting reagent, preferably 0.5% to about 6.0%, preferably 0.5% to about 4.0%, preferably 0.5% to about 2%, more preferably about 1.0%. In some embodiments, the ligand is triphenylphosphine ($PPh_3$). Suitable palladium compounds include, but are limited to palladium(II) acetate ($Pd(OAc)_2$) and palladium(II) chloride ($PdCl_2$). Suitable palladium catalysts include, but are not limited to, bis(triphenylphosphine) palladium(II) dichloride ($PdCl_2(Ph_3P)_2$), bis(acetato)bis(triphenylphosphine)palladium(II) ($Pd(OAc)_2(Ph_3P)_2$), [1,1'-bis(diphenylphosphino)ferrocene]dichloropalladium(II) ($PdCl_2(dppf)_2$)), tetrakis(triphenylphosphine palladium(0) ($Pd(PPh_3)_4$ and tris(dibenzylideneacetone)dipalladium(0) ($Pd_2(dba)_3$)). The concentration of the catalyst can vary. In some embodiments, the concentration is less than 4%, preferably less than 3%, preferably less than 1%. In some embodiments, the concentration of the catalyst is from about 0.1% to about 2.0% relative to the limiting reagent, preferably 0.2% to about 1.0%, more preferably about 0.3%. In some embodiments, the palladium catalyst is palladium(II) acetate and a ligand.

Scheme 3

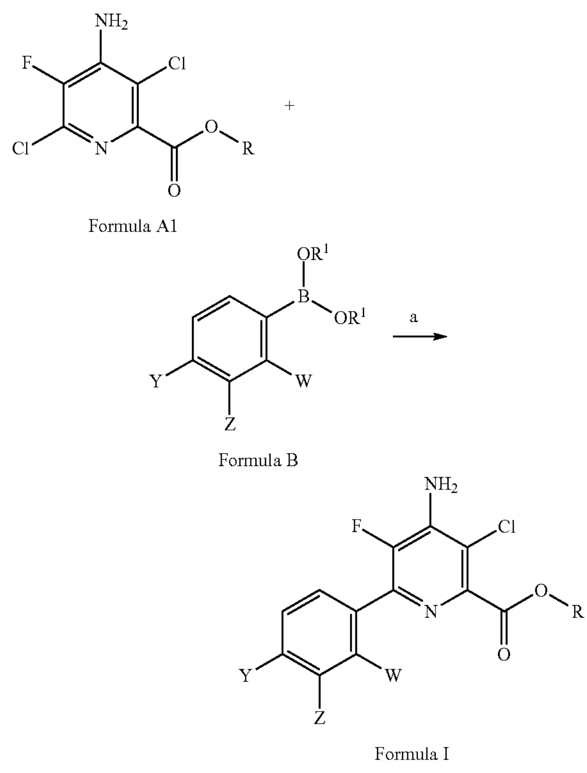

Formula A1

Formula B

Formula I

The following examples are presented to illustrate the disclosure.

EXAMPLES

Example 1: Preparation of methyl 4-amino-3,5,6-trichloropicolinate (1)

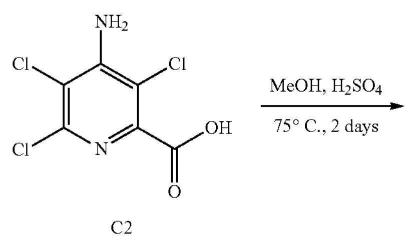

C2

-continued

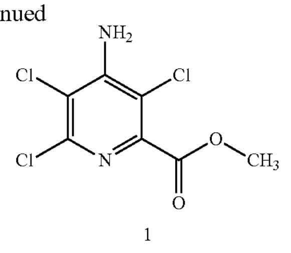

1

4-Amino-3,5,6-trichloropicolinic acid (Picloram, C2; 100 grams (g), 414 millimoles (mmol)) was suspended in methanol (800 milliliters (mL)). Concentrated sulfuric acid (26 mL, 487 mmol) was added slowly at room temperature. The reaction mixture was stirred at 75° C. (oil bath with condenser) for 2 days. The mixture was cooled to room temperature. Water (200 mL) was added. The light brown solution was concentrated to remove the solvent. The resulting residue was dissolved in water (200 mL) and ethyl acetate (EtOAc; 600 mL). The solution was cooled in an ice-bath and neutralized with 4 Normal (N) sodium hydroxide (NaOH) and saturated sodium bicarbonate ($NaHCO_3$) solution to pH=8. The organic layer was separated and the aqueous layer was washed with EtOAc. The combined organic extracts were dried and concentrated to yield the title compound as pale yellow solid (71 g, 67%, HPLC purity 99.9%): mp 125.8-126.1° C.; H NMR (400 MHz, $CDCl_3$) δ 5.38 (br s, 2H), 3.97 (s, 3H).

Example 2: Preparation of isopropyl 4-amino-3,5,6-trichloropicolinate (2)

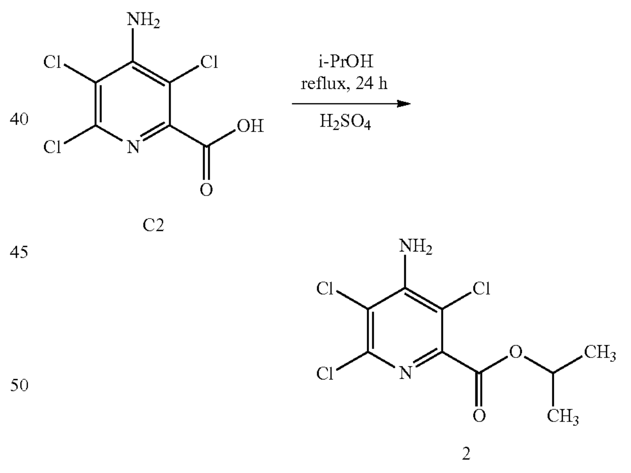

C2

2

Picloram (C2; 4.66 g, 18.3 mmol) was suspended in isopropyl alcohol (30 mL). Concentrated sulfuric acid (0.6 g, 6.1 mmol) was added at room temperature. The reaction mixture was heated at reflux for 18 hours. The reaction mixture was cooled to room temperature. Aqueous potassium carbonate ($K_2CO_3$, 23%; 10 mL) was added slowly to the reaction mixture, and the mixture was stirred for 30 minutes. The reaction mixture was extracted with EtOAc (20 mL) and the organic phase was washed with saturated, aqueous brine (20 mL). The organic phase was dried, and the solvent was evaporated. The residual solid was dried in the vacuum oven to give the title compound as an off-white solid (4.9 g, 94%, HPLC purity 96%): mp 128.5-131.0° C.; $^1H$ NMR (400 MHz, $CDCl_3$) δ 5.35 (br s, 2H), 5.29 (septuplet, J=6.4 Hz, 1H), 1.39 (d, J=6.4 Hz, 6H) ppm.

Example 3: Preparation of methyl 3,5,6-trichloro-4-(1,3-dioxoisoindolin-2-yl)picolinate (3)

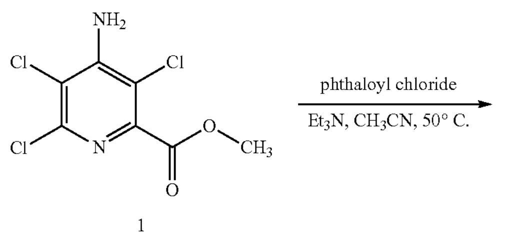

1

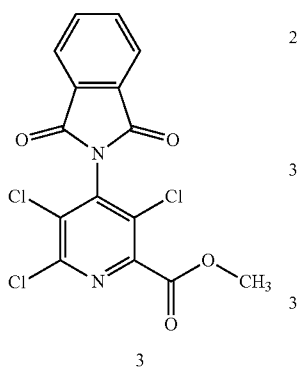

3

Methyl 4-amino-3,5,6-trichloropicolinate (1; 86 g, 337 mmol) was dissolved in acetonitrile (600 mL). Triethylamine (94 mL, 673 mmol) was added at room temperature. Phthaloyl chloride (65 mL, 404 mmol) was added dropwise. The reaction mixture was stirred at 50° C. overnight. Water (100 mL) was added to the mixture. The suspension was stirred for 1 hour and the mixture was filtered through filter paper. The solid was washed with water, then hexane, and dried. The dry solid was suspended in toluene (200 mL), and the resulting mixture was concentrated to provide the title compound as a pale yellow solid (85.1 g, 66%, HPLC purity 97.7%): mp. 185.3-185.9° C.; $^1H$ NMR (400 MHz, $CDCl_3$) δ 8.02 (m, 2H), 7.88 (m, 2H), 4.02 (s, 3H).

Example 4: Preparation of 3,5,6-trichloro-4-(1,3-dioxoisoindolin-2-yl)picolinonitrile (4)

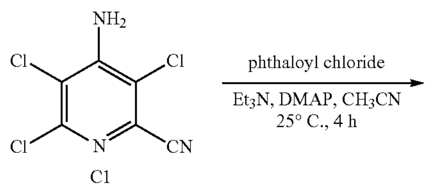

C1

-continued

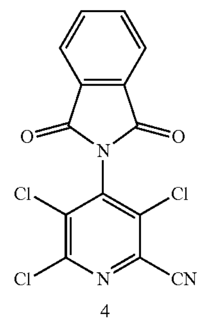

4

4-Amino-3,5,6-trichloropicolinonitrile (C1; 64.1 g, 288 mmol) was suspended in acetonitrile (960 mL). Triethylamine (90 mL, 640 mmol) and 4-(dimethylamino)pyridine (DMAP; 3.52 g, 28.8 mmol) were added at room temperature. Phthaloyl chloride (51.2 mL, 320 mmol) was added slowly, being careful to maintain an internal reaction temperature of less than 50° C. during the addition. The reaction mixture was stirred at room temperature for 4 hours. Water (130 mL) was added to the reaction mixture, and the suspension was stirred for 30 minutes. The solid was collected via filtration and washed with water (4×150 mL) and hexane (2×100 mL). The solid was dried to yield the title compound as a light purple solid (97.0 g, 96%), which was dissolved in dichloromethane and passed through a silica gel pad to give an off-white solid with an HPLC purity of 99.6%: mp 233.7-234.8° C.; $^1H$NMR (400 MHz, DMSO-$d_6$) δ 8.14 (m, 2H), 8.04 (m, 2H).

Example 5: Preparation of methyl 3,5,6-trichloro-4-(1,3-dioxoisoindolin-2-yl)picolinate (3)

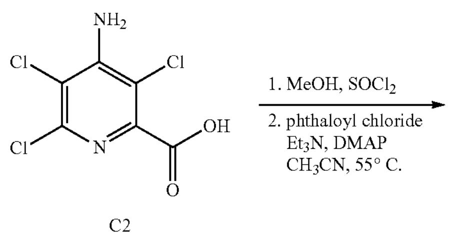

C2

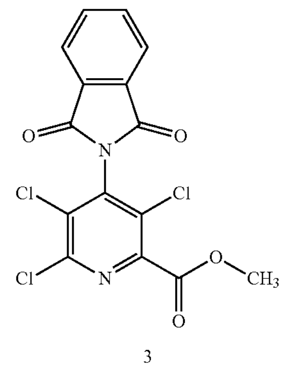

3

Picloram (C2; 105.3 g, 415 mmol) was suspended in MeOH (650 mL) in a 3-Liter (L), three-neck flask equipped with mechanical stirrer and condenser. The mixture was stirred vigorously at room temperature. Thionyl chloride (0.90 mL, 12 mmol) was added dropwise. The reaction mixture was stirred at 75° C. (external temperature) for 18 hours. The methanol was concentrated (about 150 mL remaining). Toluene (500 mL) was added and co-evaporated at 40-55° C. under house vacuum to dryness. Acetonitrile (690 mL), triethylamine (134 mL, 959 mmol), and DMAP (5.33 g, 43.6 mmol) were added. Phthaloyl chloride (77 mL, 480 mmol) was added dropwise, being careful to maintain an internal reaction temperature of less than 55° C. during the addition. After addition was complete, the reaction mixture was stirred for another 2 hours. Water (200 mL) was added to the mixture. The resulting suspension was stirred for 30 minutes and filtered. The wet cake collected on the funnel was washed with water (2×200 mL), hexanes (200 mL) and dried under vacuum. The title compound was isolated as a beige solid (154.4 g, 96% over 2 steps, HPLC purity 98%).

The following compound was prepared in like manner to the procedure outlined in Example 5:

Ethyl 3,5,6-trichloro-4-(1,3-dioxoisoindolin-2-yl) picolinate (8)

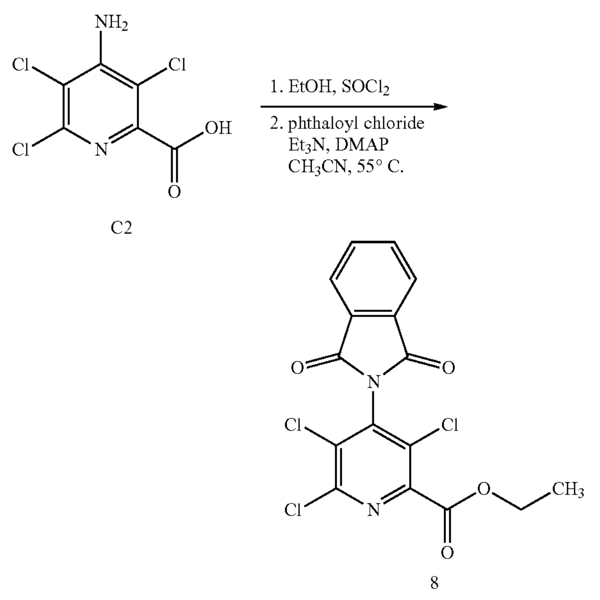

C2

8

A 500 mL round bottom flask was charged with Picloram (C2; 30 g, 122 mmol) and EtOH (200 mL). Thionyl chloride (0.43 mL, 6.1 mmol) was added dropwise. The white slurry was stirred at 75° C. for 6 hours. Additional thionyl chloride (0.43 mL, 6.1 mmol) was added. The reaction mixture was stirred at 75° C. for 16 hours. The reaction mixture was concentrated to yield yellow oil, which was co-evaporated with acetonitrile (2×200 mL) to dryness to give a white solid. The white solid was dissolved in acetonitrile (200 mL). Triethylamine (37.4 mL, 268 mmol), DMAP (1.47 g, 12.2 mmol), and phthaloyl chloride (19.3 mL, 134 mmol) were added sequentially. The temperature was lower than 58° C. during the addition. The reaction mixture was stirred at room temperature for 2 hours, quenched with water (60 mL), and filtered. The filtrate was washed with water and hexanes and dried to provide the title compound (43.3 g, 89%, HPLC purity 99.4%): $^1H$ NMR (400 MHz, $CDCl_3$) 8.10 (m, 2H), 7.87 (m, 2H), 4.47 (q, J=7.2 Hz, 2H), 1.43 (t, J=7.2 Hz, 3H).

Example 6: Preparation of isopropyl 3,5,6-trichloro-4-(1,3-dioxoisoindolin-2-yl)picolinate (5)

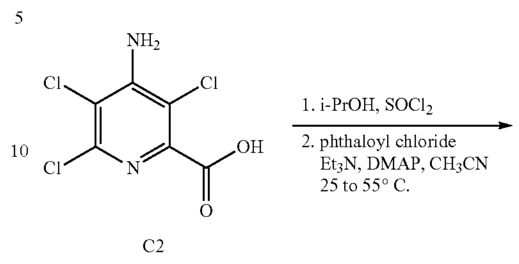

C2

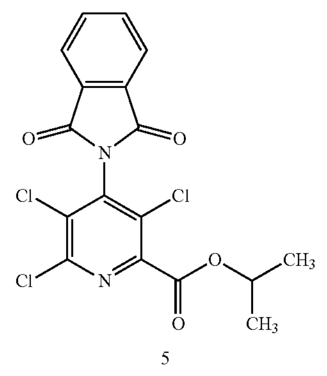

5

Step 1: A 3-L, three-neck flask equipped with mechanical stirrer, condenser, and addition funnel was charged with Picloram (C2; 100 g, 414 mmol) and isopropyl alcohol (950 mL). Thionyl chloride (15.1 mL, 207 mmol) was added to the slurry dropwise via addition funnel at room temperature, and the reaction mixture was heated at reflux for 24 h. The reaction mixture was cooled to room temperature and concentrated to dryness. The residue was co-evaporated with acetonitrile (2×100 mL) to yield a white solid (117.5 g), which is a mixture of 2 (93.6%) and Picloram (2.84%) by HPLC.

Step 2: A 3-L, three-neck flask equipped with mechanical stirrer, thermometer, and addition funnel was charged with the white solid isolated above, acetonitrile (700 mL), triethylamine (150 mL, 1.077 moles (mol)) and DMAP (5.05 g, 41.4 mmol). Phthaloyl chloride (90%; 73 mL, 456 mmol) was added dropwise via addition funnel to maintain the temperature below 55° C. The reaction mixture was stirred at room temperature for 3 hours. Water (250 mL) was added to the mixture. The resulting suspension was stirred for 30 minutes and filtered through filter paper. The solid was washed with water (3×100 mL) and hexane (2×100 mL) and dried. The solid was co-evaporated with toluene (2×250 mL), dried, washed with hexanes (2×200 mL) and dried again. The title compound was isolated as a pale, yellow solid ((151.5 g, 88%, HPLC purity 98.8%): mp 157.0-157.9° C.; $^1H$ NMR (400 MHz, $CDCl_3$) δ 8.04-8.00 (m, 2H), 7.90-7.86 (m, 2H), 5.33 (septuplet, J=6.4 Hz, 1H), 1.42 (d, J=6.4 Hz, 6H).

Example 7: Preparation of isopropyl 3,5,6-trichloro-4-(1,3-dioxoisoindolin-2-yl)picolinate (5)

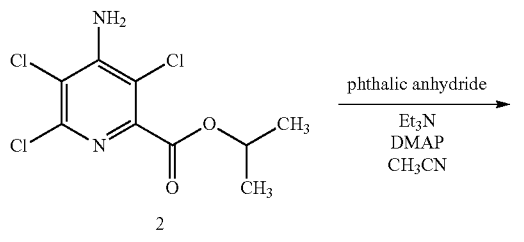

2

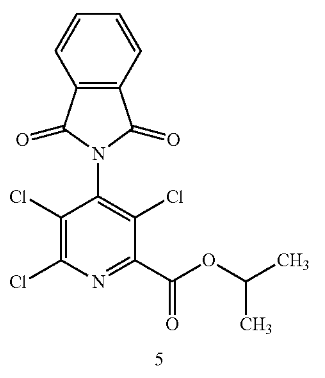

5

Compound 2 (8.1 g, 27.6 mmol) was suspended in acetonitrile (33 mL) in a 100 mL round bottom flask equipped with a magnetic stirrer and a condenser. Triethylamine (9.6 mL, 69.0 mmol) and phthalic anhydride (4.9 g, 33.1 mmol) were added at room temperature. DMAP (0.34 g, 2.76 mmol) was then added. The yellow suspension was stirred at 80° C. (oil bath temperature) for 2 hours. Additional phthalic anhydride (4.0 g, 27.0 mmol) was added to the reaction mixture at 80° C. The reaction mixture was stirred at 80° C. for another 4.5 hours. (Total reaction time was 6.5 hours.) The reaction mixture was cooled to room temperature, and water (33 mL) was added to the mixture. The suspension was stirred for 30 minutes and filtered through filter paper. The wet solid was washed with water and hexane and dried at 55° C. in a vacuum oven. The title compound was isolated as a yellow solid (9.8 g, 86%, HPLC purity 99.2%).

Example 8: Preparation of isopropyl 3,5,6-trichloro-4-(1,3-dioxoisoindolin-2-yl)picolinate (5)

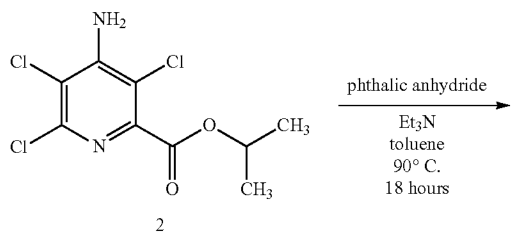

2

-continued

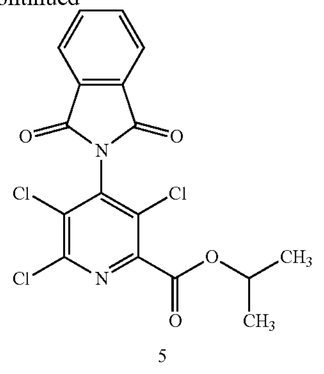

5

To a suspension of compound 2 (2.5 g, 8.82 mmol) in toluene (11 mL) were added triethylamine (2.96 mL, 21.2 mmol) and phthalic anhydride (3.26 g, 22.0 mmol). The resulting suspension was stirred in a 90° C. oil bath for 18 hours. The clear yellow solution was cooled gradually to room temperature to provide a thick beige slurry. Saturated sodium bicarbonate solution (5 mL) was added slowly at room temperature, and the resulting slurry was stirred in an ice-water bath for 1 hour. The solid was collected by vacuum filtration and was washed with water (2×5 mL). The wet solid was dried in a vacuum oven at 55° C. for 5 hours. The title compound was isolated as an off-white powdery solid (3.1 g, 86%, HPLC purity 99.5%).

Example 9: Preparation of isopropyl 3,5,6-trichloro-4-(1,3-dioxoisoindolin-2-yl)picolinate (5)

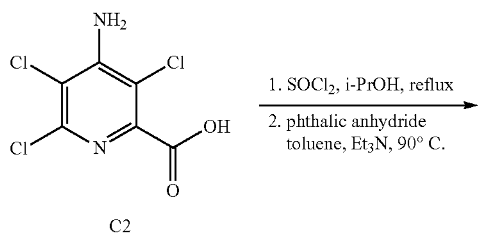

C2

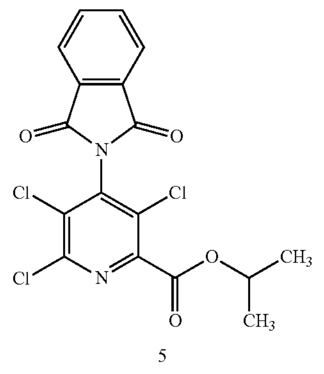

5

A 2-L flask was charged with Picloram (C2; 101.8 g, 98.2% purity, 0.414 mol) and isopropyl alcohol (918.3 mL). Thionyl chloride (15.6 mL, 97% purity, 0.21 mol) was added, and the reaction mixture was heated at reflux for 17 hours. The isopropyl alcohol (750 mL) was distilled off under atmospheric pressure. Toluene (600 mL) was added to the resulting solution. Distillation was continued, and after another 2 hours, a mixture of isopropyl alcohol/toluene (600 mL) was distilled off at 81-110° C. To the stirred suspension were added sequentially triethylamine (144.3 mL, 1.04 mol) and phthalic anhydride (153.3 g, 1.04 mol) in portions. The reaction mixture was heated at 88-93° C. for 17 hours and cooled to room temperature. Saturated aqueous sodium bicarbonate (400 mL) was added slowly over 0.5 hours with cooling to keep the temperature below 20° C. The resultant slurry was stirred at room temperature for 2 hours and filtered. The solid was washed with water (3×100 mL) and dried at 60° C. for 24 h to afford the title compound (144 g, 84%, HPLC purity 99%).

Example 10: Preparation of cyclohexyl 3,5,6-trichloro-4-(1,3-dioxoisoindolin-2-yl)picolinate (10)

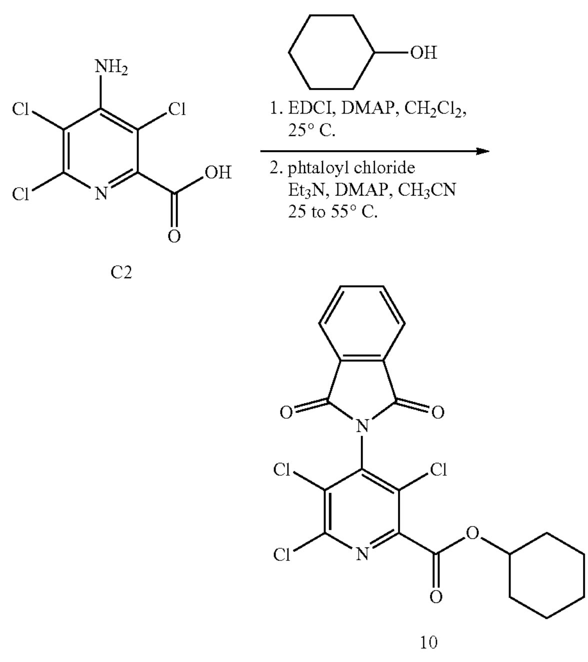

C2

10

Step 1: To a mixture of Picloram (C2; 20 g, 82.8 mmol), DMAP (5.06 g, 41.4 mmol), and hexanol (7.88 g, 78.7 mmol) in dichloromethane (200 mL) was added N-(3-dimethylaminopropyl)-N-ethylcarbodiimide hydrochloride (EDCI; 17.5 g, 91.1 mmol) in four portions. The white slurry was stirred at room temperature for 16 hours, filtered through a silica pad directly, and washed with dichloromethane (3 L). The product fraction was combined to yield the ester (16.2 g, 60%).

Step 2: To a mixture of the ester from Step 1 (16.2 g, 50.1 mmol), DMAP (0.61 g, 5.01 mmol), and triethylamine (15.4 mL, 110 mmol) in acetonitrile (100 mL) was added phthaloyl chloride (7.9 mL, 55.1 mmol) slowly. The yellow suspension was stirred vigorously for 2 hours, quenched with water (100 mL), filtered and washed with methanol. The solid was co-evaporated with toluene, filtered, and washed with hexanes to give compound the title compound (19 g, 84%) with some toluene. This solid was further purified through a silica gel column (12.9 g, 57%, HPLC purity 99.1%): $^1$H NMR (400 MHz, $CDCl_3$) 8.01 (m, 2H), 7.88 (m, 2H), 5.11 (m, 1H), 2.02 (m, 2H), 1.79 (m, 2H), 1.64 (m, 3H), 1.40 (m, 2H), 1.33 (m, 1H).

Example 11: Preparation of benzyl 3,5,6-trichloro-4-(1,3-dioxoisoindolin-2-yl)picolinate (12)

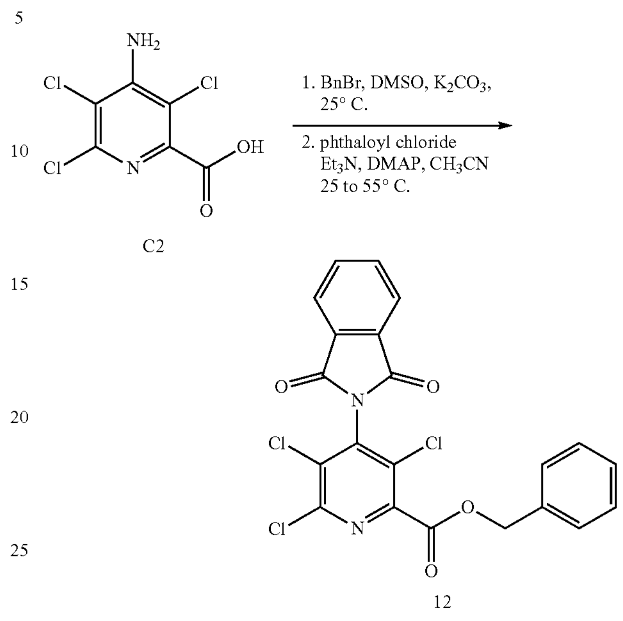

C2

12

Step 1: To a mixture of Picloram (C2; 5.0 g, 19.7 mmol) and potassium carbonate (3.27 g, 23.7 mmol) in DMSO (5 mL) was added benzyl bromide (BnBr; 2.81 mL, 23.7 mmol). The reaction mixture was stirred at room temperature for 4 hours, quenched with water, filtered to provide solid, which was dissolved in EtOAc (50 mL) and precipitated out by adding hexanes (50 mL). The solid was used in the next step without further manipulation.

Step 2: To a suspension of the solid from Step 1 in acetonitrile (35 mL) were added sequentially triethylamine (6.0 mL, 43.1 mmol), DMAP (0.24 g, 1.98 mmol), and phthaloyl chloride (3.47 mL, 21.7 mmol). The reaction mixture was stirred at room temperature for 3 hours, quenched with water, filtered, and washed with water and hexanes and dried to provide the title compound (7.41 g, 81%, HPLC purity 97.1%): $^1$H NMR (400 MHz, $CDCl_3$) 8.01 (m, 2H), 7.88 (m, 2H), 7.46 (m, 2H), 7.36 (m, 3H), 5.45 (s, 2H).

Example 12: Preparation of methyl 3-chloro-4-(1,3-dioxoisoindolin-2-yl)-5,6-difluoropicolinate (6)

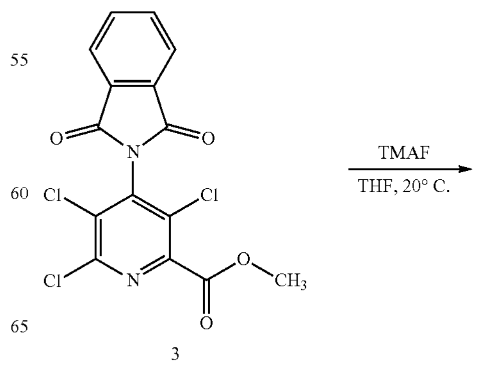

TMAF

THF, 20° C.

3

-continued

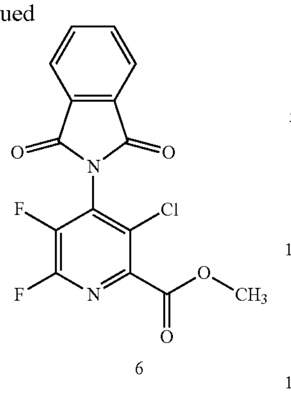

6

To compound 3 (5.00 g, 13.0 mmol) in a 250 mL round-bottom flask under nitrogen were added anhydrous tetrahydrofuran (THF; 100 mL) and tetramethylammonium fluoride (TMAF, Aldrich; 4.83 g, 51.87 mmol) in one portion. The reaction mixture was stirred at room temperature for 5 hours, cooled to 0° C., quenched with water (400 mL) and stirred at 0° C. for 1 hour. The solid was collected by filtration, washed with water (2×100 mL) and hexanes (3×100 mL), and dried. The title compound was isolated as a pale yellow solid (4.0 g, 87%, HPLC purity 92.3%): mp 180.2-182.6° C.; $^1H$ NMR (DMSO-$d_6$) δ 8.12 (d, 2H), 8.02 (d, 2H), 3.94 (s, 3H); $^{19}F$ NMR δ −83.30, −133.05. Also contained 6.6% of the 3,5,6-trifluorinated side-product.

Example 13: Preparation of methyl 3-chloro-4-(1,3-dioxoisoindolin-2-yl)-5,6-difluoropicolinate (6)

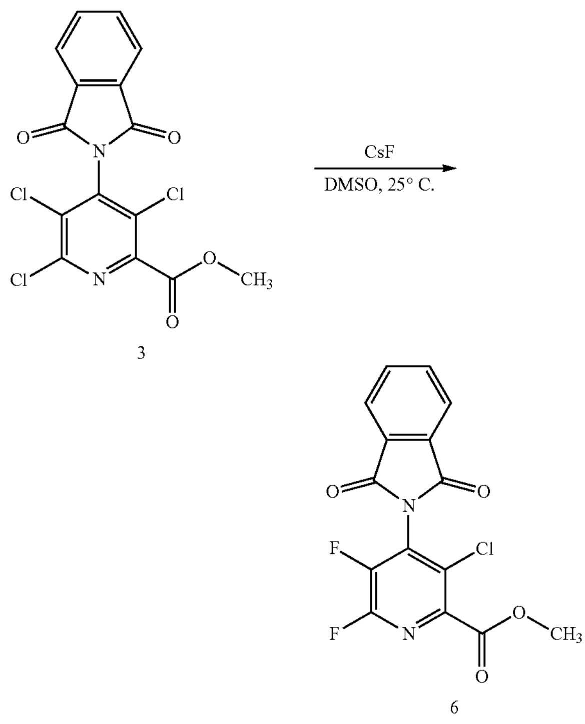

3

6

A mixture of cesium fluoride (CsF; 82.7 g, 545 mmol) in dimethyl sulfoxide (DMSO; 1.2 L) was distilled at 90° C. under house vacuum to remove DMSO (250 mL). After cooling to room temperature under nitrogen ($N_2$), compound 3 (60.0 g, 156 mmol) was added in three portions. The mixture was stirred vigorously under $N_2$ for 27 hours at 25° C., poured into ice water (3.6 L), stirred for 1 hour, and filtered. The filtered solid washed with water (600 mL) and hexanes (300 mL), and dried to provide the title compound as an off-white solid (55 g, 100% (not purified), HPLC purity 93.6% (also containing 1.3% monofluoro side-product and 2.3% trifluoro side-product). The off-white solid was stirred at reflux in methanol (150 mL) for 30 minutes and filtered to give the title compound as a pale, beige solid (51.1 g, 92.7% yield, HPLC purity 95.7% (also containing 1.3% 6-monofluoro side-product and 1.7% 3,5,6-trifluoro side-product).

A sample of the pale, beige solid from above (1.0 g) was dissolved in a minimum amount of hot ethyl acetate (12.5 mL), and the resulting solution was diluted with methanol (25 mL). The resulting solution was gradually cooled with stirring to room temperature and then was cooled in an ice-water bath. The mixture that formed was filtered, and the filtered solid was washed twice with methanol (5 mL) and dried. The title compound was isolated as off-white, fine crystals (0.81 g, 81% recovery, HPLC purity 98.1%, also containing 0.8% 6-monofluoro side-product and 0.9% 3,5,6-trifluoro side-product.

Example 14: Preparation of isopropyl 3-chloro-4-(1,3-dioxoisoindolin-2-yl)-5,6-difluoropicolinate (7)

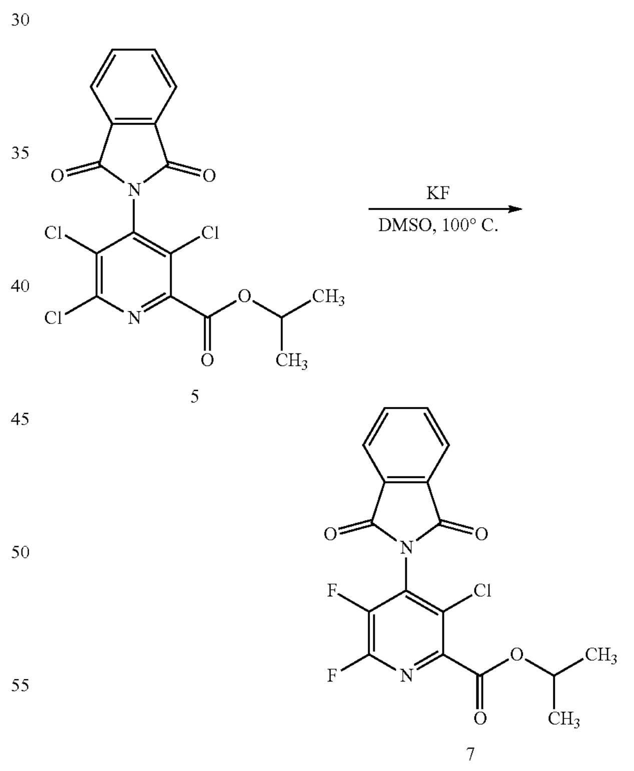

5

7

Solid potassium fluoride (KF, Sigma Aldrich; 12.7 g, 219 mmol) was added to a 1-L jacketed glass reactor which had been purged with nitrogen and was maintained under an atmosphere of nitrogen. The reactor was fitted with a 1-inch diameter, trayed distilling column. DMSO (Fisher Scientific; 353.0 g) was added to the reactor. The mixture was agitated at a rate of 350 revolutions per minute (RPM). A vacuum of approximately 40 millimeters of mercury (mmHg) was applied and the temperature of the reactor contents was increased to approximately 108° C. Approximately 100 mL of material was distilled with the distilling column and removed from the reactor. The temperature of the reactor contents was reduced to 75° C., and the water content was determined by Karl Fischer analysis to be 51 parts per million (ppm). The reactor was charged with compound 5 (24.9 g, 60.2 mmol) and the temperature was increased to 100° C. The reaction was held at 100° C. for approximately 7.5 hours. The reactor was cooled to 75° C. and the reaction mixture was passed through a fritted filter to remove the solids. The filtered salts were washed with DMSO (44 g), and the filtrate and wash were added to a second vessel for crystallization. The second vessel was cooled to 12° C., the contents were agitated at 250 RPM, and water (363 g) was added continuously to the second vessel over approximately 2 hours. A mixture formed and was stirred for an additional hour at 12° C. The solid was collected by filtration, washed with water (about 68 g), and dried in a vacuum oven at 60° C. (25 torr) overnight. The resulting dry solid (21.5 g, 94%) provided 93.7% of the title compound, 2.6% of the 3,5,6-trifluoro side-product, and 2.0% of the 6-monofluoro side-product: mp 115.8-117.1° C.; H NMR (400 MHz, $CDCl_3$) δ 8.00-8.06 (m, 2H), 7.91-7.86 (m, 2H), 5.32 (septet, J=6.0 Hz, 1H), 1.42 (d, J=6.0 Hz, 6H); $^{19}F$ NMR (376 MHz, $CDCl_3$) δ −134.21 (d), −82.76 (d).

Example 15: Preparation of isopropyl 3-chloro-4-(1,3-dioxoisoindolin-2-yl)-5,6-difluoropicolinate (7)

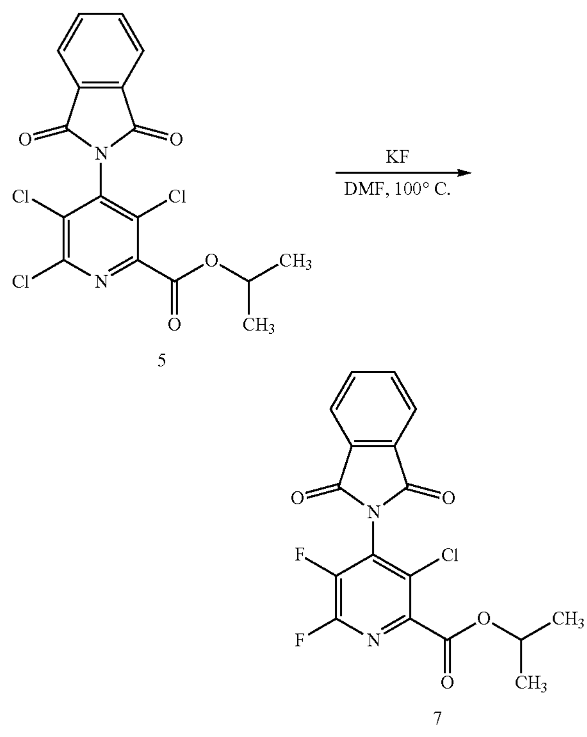

5

7

Solid potassium fluoride (Sigma Aldrich; 7.68 g, 132 mmol) was added to a 1-L jacketed glass reactor which had been purged with nitrogen and was maintained under an atmosphere of nitrogen. The reactor was fitted with a 1-inch diameter, trayed distilling column containing 7 trays. DMF (Fisher Scientific, 211.7 g) and toluene (Fisher Scientific, 41.6 g) were added sequentially to the reactor. The solution was agitated at a rate of 275 RPM. A vacuum of approximately 350 mmHg was applied, and the temperature of the reactor contents was increased to approximately 110° C. Approximately 75 mL of material was distilled with the distilling column and removed from the reactor by decreasing the pressure as material was distilled overhead. The temperature of the reactor contents was reduced to 45° C., and the water content was determined by Karl Fischer analysis to be 101 ppm. The reactor was charged with compound 5 (15.2 g, 36.7 mmol), and the temperature was increased to 100° C. The reaction was held at 100° C. for approximately 33 hours. The reactor was cooled to 40° C. and the reaction mixture was passed through a fritted filter to remove the solid salts. The filtered salts were washed with DMF (36.1 g) and the filtrate and wash were added to a second vessel for crystallization. The second vessel was cooled to 10° C., the contents were agitated at 250 RPM, and water (170 g) was added continuously over approximately 2 hours. A mixture formed and was stirred for another 4 hours at 10° C. The solid was collected by filtration, washed with water (about 44 g), and dried in a vacuum oven at 60° C. (25 torr) overnight. The resulting dry solid (12.0 g, 80%) provided 82.6% of the title compound, 1.1% of the 3,5,6-trifluoro side-product, and 16.6% of the 6-monofluoro side-product.

Example 16: Preparation of isopropyl 3-chloro-4-(1,3-dioxoisoindolin-2-yl)-5,6-difluoropicolinate (7)

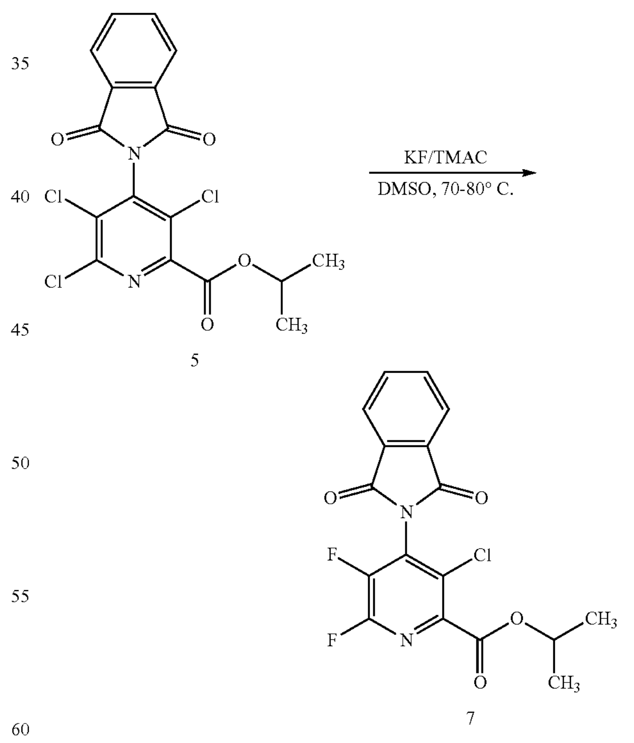

5

7

Solid potassium fluoride (Sigma Aldrich; 11.2 g, 192 mmol) was added to a 1-L jacketed glass reactor which had been purged with nitrogen and was maintained under an atmosphere of nitrogen. The reactor was fitted with a 1-inch diameter, trayed distilling column containing 7 trays. DMSO (Fisher Scientific; 207.2 g) and solid tetramethylammonium chloride (TMAC, Sigma Aldrich; 5.29 g, 48.3 mmol) were added sequentially to the reactor. The mixture was agitated at a rate of 350 RPM. A vacuum of approximately 100 mmHg was applied, and the temperature of the reactor contents was increased to approximately 100° C. Approximately 35 mL of material was distilled with the distilling column and removed from the reactor. The temperature of the reactor contents was reduced to 45° C., and the water content was determined by Karl Fischer analysis to be 102 ppm. The reactor was charged with compound 5 (19.8 g, 47.9 mmol), and the temperature of the reaction mixture was increased to 60° C. The reaction was held at 60° C. for approximately 3.5 hours and then was increased to 70° C. That temperature was held for approximately 8.5 hours at 70° C. and was increased and held for one hour at 80° C. The reactor was cooled to 75° C. and the reaction mixture was passed through a fritted filter to remove the solid salts. The filtered salts were washed with DMSO (50 g) and the filtrate and wash were added to a second vessel for crystallization. The second vessel was cooled to 21° C., the contents were agitated at 250 RPM, and water (267 g) was added continuously over approximately 2 hours. A mixture formed and was stirred for another one hour at 21° C., and the solid present was then collected by filtration, washed with water (about 66 g), and dried in a vacuum oven at 60° C. (25 torr) overnight. The resulting dry solid (15.5 g, 85% yield) provided 97.5% of the title compound, which also contained 1.7% of the 3,5,6-trifluoro side-product and 1.9% of the 6-monofluoro side-product.

Example 17: Preparation of isopropyl 3-chloro-4-(1,3-dioxoisoindolin-2-yl)-5,6-difluoropicolinate (7)

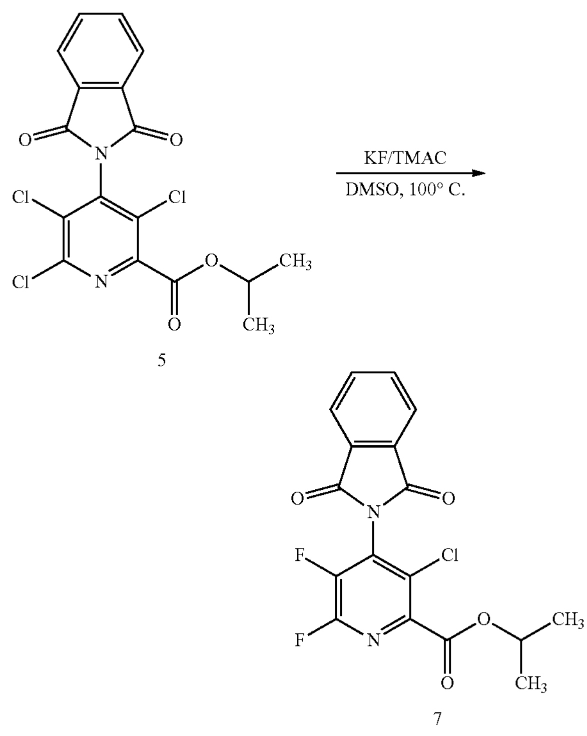

Solid potassium fluoride (Sigma Aldrich; 12.7 g, 219 mmol) was added to a 1-L jacketed glass reactor which had been purged with nitrogen and was maintained under an atmosphere of nitrogen. The reactor was fitted with a 1-inch diameter, trayed distilling column containing 7 trays. DMSO (Fisher Scientific; 408.9 g) and a solution of 35% tetramethylammonium chloride (TMAC) in methanol (SAChem; 34.6 g, 110 mmol) were added sequentially to the reactor. The mixture was agitated at a rate of 350 RPM. A vacuum of approximately 60 mmHg was applied, and the temperature of the reactor contents was increased to approximately 100° C. Approximately 115 mL of material was distilled with the distilling column and removed from the reactor. The temperature of the reactor contents was reduced to 70° C. and more DMSO (54 g) was added to the reaction mixture before restarting the distillation and collecting approximately 35 mL of additional distillate. The temperature of the reactor contents was reduced to 75° C., and the water content was determined by Karl Fischer analysis to be 179 ppm. The reactor was charged with compound 5 (24.9 g, 60.2 mmol), and the temperature was increased to 100° C. The reaction was held at 100° C. for approximately 2.25 hours. The reactor was cooled to 75° C. and the reaction mixture was passed through a fritted filter to remove the solid salts. The filtered salts were washed with DMSO (116 g) and the filtrate and wash were added to a second vessel for crystallization. The second vessel was cooled to 14° C., the contents were agitated at 250 RPM, and water (283 g) was added continuously over approximately 2 hours. A mixture formed and was stirred for an additional hour at 14° C. The solid was collected by filtration, washed with water (about 64 g), and dried in a vacuum oven at 60° C. (25 torr) overnight. The resulting dry solid (22.5 g, 98%) provided 98.3% of the title compound, 3.8% of the 3,5,6-trifluoro side-product, and 0.5% of the 6-monofluoro side-product.

Example 18: Preparation of ethyl 3-chloro-4-(1,3-dioxoisoindolin-2-yl)-5,6-difluoropicolinate (9)

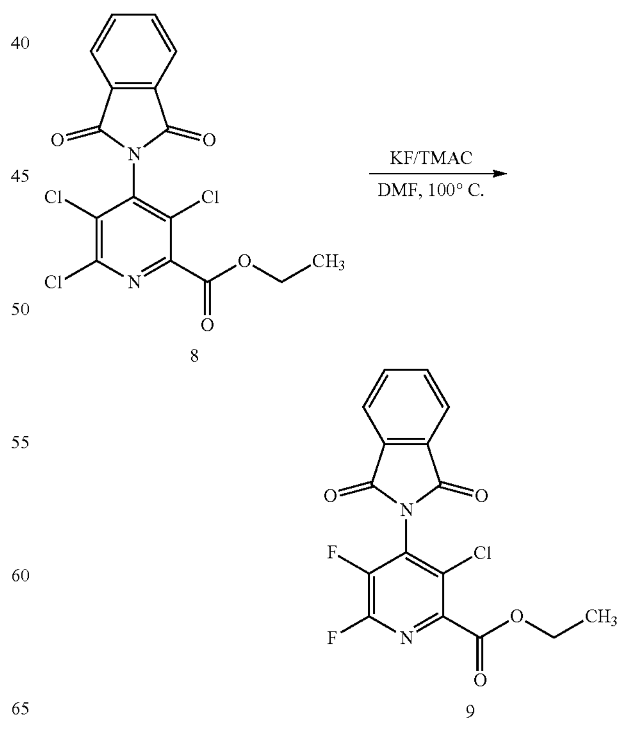

Solid potassium fluoride (Sigma Aldrich; 5.9 g, 102 mmol; Sigma Aldrich) was added to a 1-L jacketed glass reactor which had been purged with nitrogen and was maintained under an atmosphere of nitrogen. The reactor was fitted with a 1-inch diameter, trayed distilling column containing 7 trays. DMF (Fisher Scientific; 139.5 g) and a solution of 35% tetramethylammonium chloride (TMAC) in methanol (SAChem; 15.8 g, 50.4 mmol) were added sequentially to the reactor. The solution was agitated at a rate of 350 RPM. A vacuum of approximately 90 mmHg was applied, and the temperature of the reactor contents was increased to approximately 90° C. Approximately 75 mL of material was distilled with the distilling column and removed from the reactor. The temperature of the reactor contents was reduced to 45° C., and the water content was determined by Karl Fischer analysis to be 105 ppm. The reactor was charged with compound 8 (10.1 g, 25.1 mmol), and the temperature was increased to 100° C. The reaction was held at 100° C. for approximately 4 hours. The reactor was cooled to 50° C. and the reaction mixture was passed through a fritted filter to remove the solid salts. The filtered salts were washed with DMF (73 g) and the filtrate and wash were added to a second vessel for crystallization. The second vessel was cooled to 2° C., the contents were agitated at 250 RPM, and water (172.3 g) was added continuously to the reaction mixture over approximately 2 hours in order to keep the temperature of the mixture below 10° C. A mixture formed and was stirred for an additional hour at about 10° C. The solid was collected by filtration, washed with water (about 35 g), and dried in a vacuum oven at 60° C. (25 torr) overnight. The resulting dry solid (6.44 g, 70%) provided 97.3% of the title compound, 2.4% of the 3,5,6-trifluoro side-product and 3.8% of the 6-monofluoro side-product: mp 111.2-116.7° C.; $^{1}H$ NMR (400 MHz, $CDCl_3$) δ 8.04-8.00 (m, 2H), 7.90-7.88 (m, 2H), 4.47 (q, J=6.8 Hz, 2H), 1.43 (d, J=6.8 Hz, 3H); $^{19}F$ NMR (376 MHz, $CDCl_3$) −133.57 (d), −82.54 (d).

Example 19: Preparation of cyclohexyl 3-chloro-4-(1,3-dioxoisoindolin-2-yl)-5,6-difluoropicolinate (11)

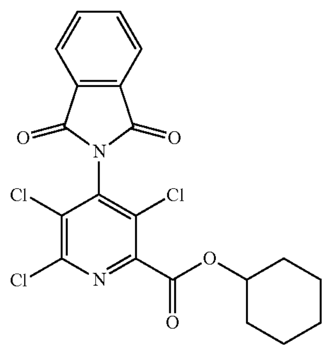

10

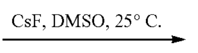

-continued

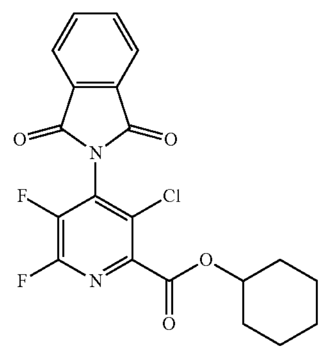

11

Cesium fluoride (1.17 g, 7.70 mmol) was added to a 50-mL round bottom flask equipped with stirring bar and distillation apparatus. DMSO (25 mL) was added. The flask was placed in an oil bath, and a vacuum (approximately 1 mm Hg) was applied to the system. DMSO (approximately 10 mL) was distilled. The distillation apparatus was removed, and the system was cooled under a nitrogen balloon. When the oil bath reached 25° C., compound 10 (1.0 g, 2.17 mmol) was added in one portion. The reaction mixture was stirred at room temperature under a nitrogen atmosphere for 24 hours, poured into 50 mL ice-water, and stirred for 30 minutes. The product was collected, and the wet cake was washed with water (2×10 mL) and hexane (10 mL) and dried in a vacuum oven at 55° C. The title compound was isolated as a yellow solid (0.89 g, 95%, HPLC purity 92.9%): $^{19}F$ NMR (376 MHz, DMSO-$d_6$) δ −83.3 (d, J=26.7 Hz), −133.7 (d, J=26.7 Hz). Also contained 2.1% of the 3,5,6-trifluoro side-product.

Example 20: Preparation of benzyl 3-chloro-4-(1,3-dioxoisoindolin-2-yl)-5,6-difluoropicolinate (13)

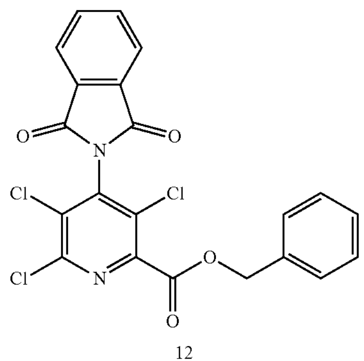

12

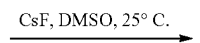

-continued

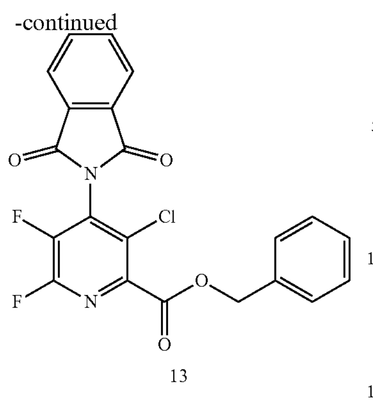

13

Cesium fluoride (1.15 g, 7.58 mmol) was added to a 50-mL round bottom flask equipped with stirring bar and distillation apparatus. DMSO (25 mL) was added. The flask was placed in an oil bath, and a vacuum (approximately 1 mm Hg) was applied to the system. DMSO (approximately 10 mL) was distilled. The distillation apparatus was removed and the system was cooled under a nitrogen balloon. Compound 12 (1.0 g, 2.17 mmol) was added in one portion. The reaction mixture was stirred at room temperature for 24 hours, poured into 50 mL ice-water, and stirred for 30 minutes. The product was collected, and the wet cake was washed with water (2×10 mL) and hexane (10 mL) and dried in a vacuum oven at 55° C. The title compound was isolated as a beige solid (0.86 g, 93%, HPLC purity 88.4%): $^{1}H$ NMR (400 MHz, DMSO-$d_6$) δ 8.18-8.10 (m, 2H), 8.06-8.00 (m, 2H), 7.45 (m, 2H), 7.42-7.30 (m, 3H), 5.42 (s, 2H); $^{19}F$ NMR (376 MHz, DMSO-$d_6$) δ −83.2 (d, J=26.7 Hz), −133.0 (d, J=26.7 Hz). Also contained 0.7% of the 6-monofluoro side-product and 7.6% of the 3,5,6-trifluoro side product.

Example 21: Preparation of 4-amino-3,6-dichloro-5-fluoropicolinic acid (14)

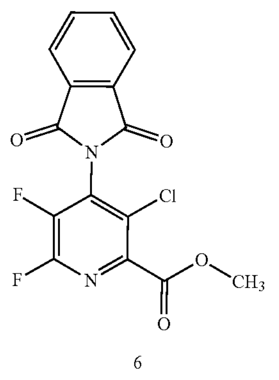

6

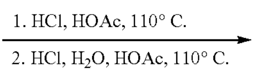

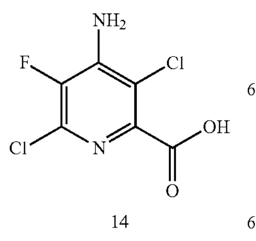

14

Compound 6 (5.0 g, 14.2 mmol) was suspended in a solution of hydrogen chloride (HCl) in acetic acid (HOAc, 2 M; 35.5 mL, 71 mmol) in a 450 mL sealed flask. The mixture was stirred at 110° C. (oil bath) overnight and was cooled to 5° C. Aqueous HCl (12 N, 10 mL) was added slowly to the flask; the flask was sealed again and put into a 110° C. oil bath overnight. The resulting mixture was cooled to 5° C. and filtered. The collected solid was suspended in 2 N aqueous HCl solution (100 mL), stirred at 110° C. for 60 minutes, and filtered. The filtered solid was washed with hexane and dried. The title compound was isolated as an off-white solid (1.88 g, 51%, HPLC purity 97.1%): mp: 211.0-212.7° C.; $^{1}H$ NMR (DMSO-$d_6$) δ 13.81 (br s, 1H), 7.21 (br s, 2H); $^{19}F$ NMR (DMSO-$d_6$) δ −137.05.

Example 22: Preparation of 4-amino-6-bromo-3-chloro-5-fluoropicolinic acid (Formula A1)

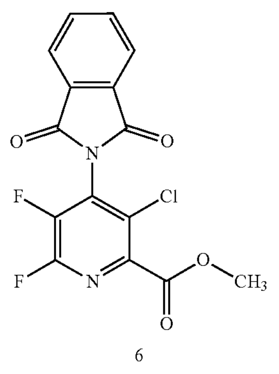

6

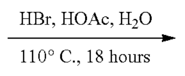

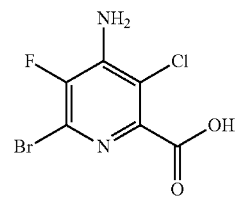

Formula A1

A mixture of compound 6 (3.92 g, 11.1 mmol), water (2 mL, 111 mmol) and anhydrous hydrogen bromide (HBr) in HOAc (5.7 M; 78 mL, 445 mmol) was heated at 110° C. for 18 hours in a 500 mL sealed flask. The reaction mixture was cooled to 0° C. and quenched with water (400 mL). The resulting suspension was stirred for 30 minutes at 0° C. and filtered, and the collected solid was washed with water (2×100 mL) and hexanes (3×100 mL). The title compound was isolated as a beige solid (2.08 g, 54%, HPLC purity 96.5%): mp 211.3-212.5° C.; $^{1}H$ NMR (DMSO-$d_6$) δ 13.72 (br s, 1H), 7.16 (br s, 2H); $^{19}F$ NMR (DMSO-$d_6$) δ −130.28.

Example 23: Preparation of 4-amino-6-bromo-3-chloro-5-fluoropicolinic acid (Formula A1)

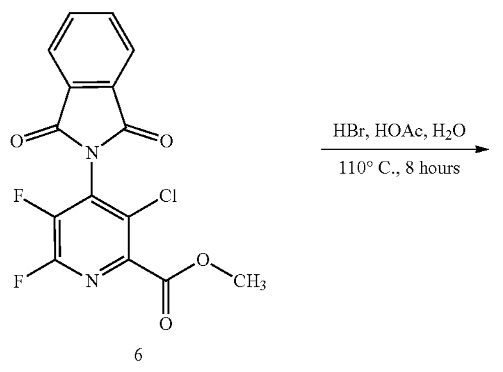

6

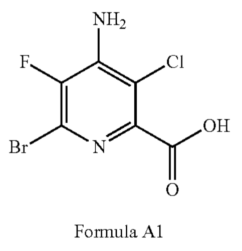

Formula A1

In a 1-L Hastelloy C276 reactor, compound 6 (50 g, 0.142 mol) was suspended in water (8.93 g, 0.496 mol), and HBr (57.5 g, 0.71 mol) in acetic acid (117 g) was added. The reactor was heated to 110° C. with agitation and maintained at 110° C. for 8 hours. The reactor was cooled to 60° C. and filtered. The wet cake was washed with water (2×150 mL) and dried. The title compound was isolated as an off-white solid (42.6 g, 90%, 90% purity).

Example 24: Preparation of 4-amino-6-bromo-3-chloro-5-fluoropicolinic acid (Formula A1)

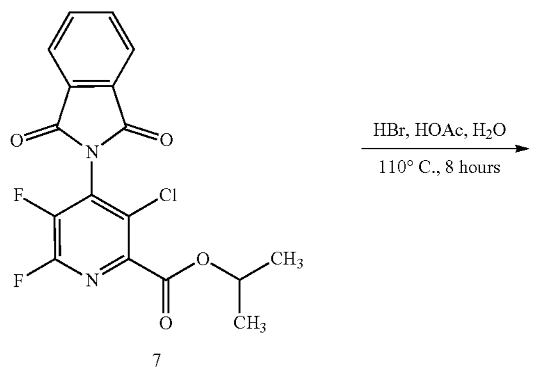

7

-continued

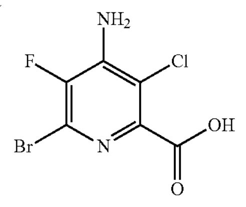

Formula A1

In a 1-L Hastelloy C276 reactor, compound 7 (50 g, 0.13 mol) was suspended in water (8.25 g, 0.46 mol), and HBr (53.0 g, 0.65 mol) in acetic acid (108 g) was added. The reactor was heated to 110° C. with agitation and maintained at 110° C. for 8 hours. The reactor was cooled to 60° C. and filtered. The wet cake was washed with water (2×150 mL) and dried. The title compound was isolated as an off-white solid (39.3 g, 90%, HPLC purity 90%).

Example 25: Preparation of 4-amino-6-bromo-3-chloro-5-fluoropicolinic acid (Formula A1)

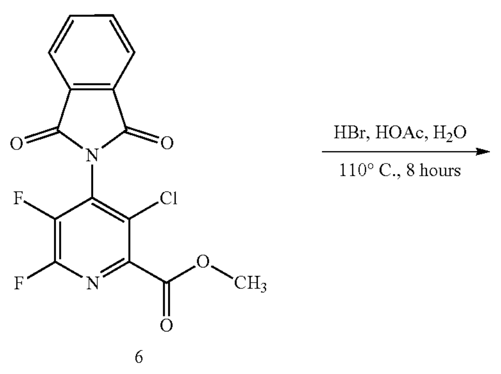

6

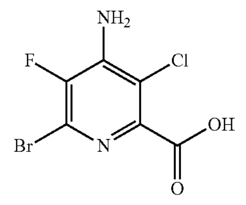

Formula A1

In a 1-L Hastelloy C276 reactor, compound 6 (50 g, 0.142 mol) was suspended in a mixture of water (8.93 g, 0.496 mol) and a solution of HBr (57.5 g, 0.71 mol) in acetic acid (117 g). The reactor was heated to 110° C. with agitation, maintained at temperature for 8 hours, cooled to 60° C., and filtered. The filtered wet cake was reslurried in 50 weight percent (wt %) aqueous methanol (150 g) at 60° C. for 1 hour and filtered. The wet cake was dried to provide the title compound as an off-white solid (33.7 g, 88%, HPLC purity 99.1%).

Example 26: Preparation of 4-amino-6-bromo-3-chloro-5-fluoropicolinic acid (Formula A1)

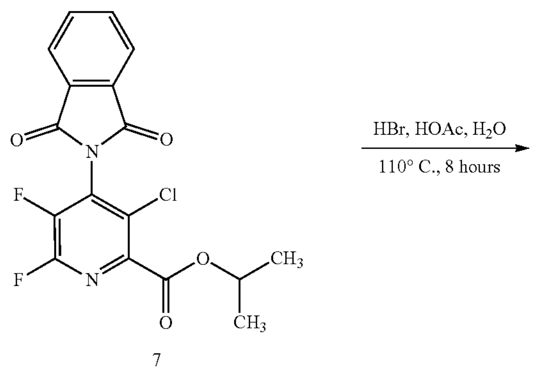

7

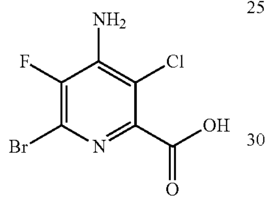

Formula A1

In a 1-L Hastelloy C276 reactor, compound 7 (50 g, 0.13 mol) was suspended in a mixture of water (8.25 g, 0.46 mol) and a solution of HBr (53.0 g, 0.65 mol) in acetic acid (108 g). The reactor was heated to 110° C. with agitation, maintained at temperature for 8 hours, cooled to 60° C., and filtered. The filtered wet cake was reslurried in 50 wt % aqueous methanol (150 g) at 60° C. for 1 hour and filtered. The wet cake was dried to provide the title compound as an off-white solid (31.4 g, 88%, HPLC purity 99.0%).

Example 27: Preparation of 4-amino-6-bromo-3-chloro-5-fluoropicolinic acid (Formula A1)

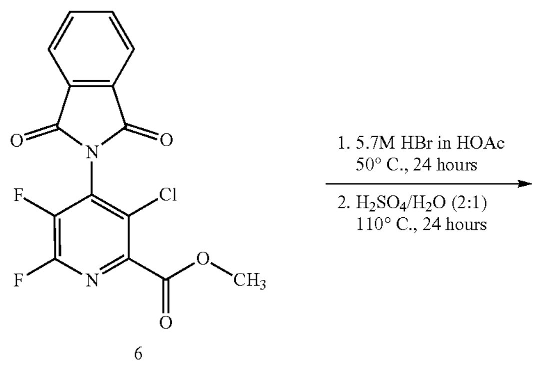

6

-continued

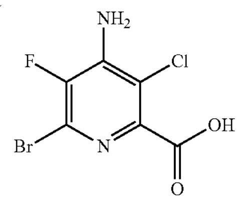

Formula A1

Step 1: A Chemglass high pressure vessel (75 mL) equipped with magnetic stirrer was charged with compound 6 (5.0 g, 14.2 mmol) and HBr in HOAc (5.7 M; 25 mL, 142 mmol). The flask was sealed with a PTFE cap and heated at 50° C. for 24 hours. The reaction mixture was cooled to 0° C. and quenched with water (50 mL). The suspension was stirred for 30 minutes at room temperature and filtered. The solid was washed with water (2×30 mL) and dried.

Step 2: To the resultant mixture from Step 1 was added a mixture of sulfuric acid and water ($H_2SO_4/H_2O$, 2:1 (v/v); 40 mL). The mixture was stirred at 110° C. for 24 hours, cooled to 0° C., and quenched with water (200 mL). The suspension was stirred for 30 minutes at room temperature and filtered. The solid was suspended in water (200 mL), and the mixture was heated at 110° C. for 1 hour. The hot suspension was filtered and dried to obtain the title compound (2.67 g, 70% over 2 steps, HPLC purity 90.3%).

Example 28: Preparation of 4-amino-3,6-dichloro-5-fluoropicolinic acid (14)

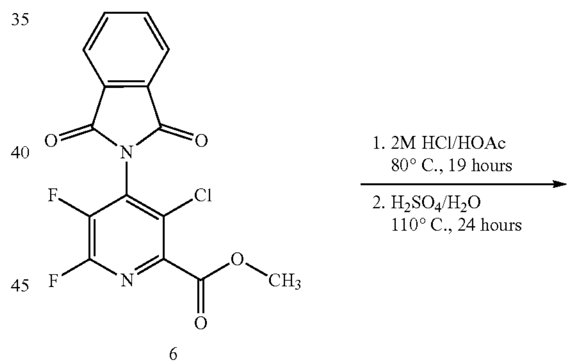

6

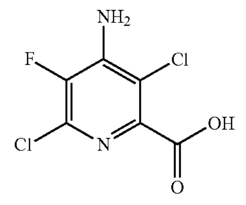

14

Step 1: Compound 6 (2.5 g, 7.1 mmol) was suspended in HCl in HOAc (2 M; 17.5 mL, 35 mmol) in a 75 mL glass, sealed flask. The mixture was stirred at 80° C. (oil bath) for 19 hours. The reaction mixture was cooled to 5° C. and poured into ice-water (60 mL). The mixture was stirred for 30 minutes and filtered. The white solid (4.5 g, wet) was used in the next reaction without further purification.

Step 2: To the mixture from Step 1 was added a mixture of $H_2SO_4/H_2O$ (2:1 v/v; 20 mL). The mixture was stirred at 110° C. for 24 hours, cooled to 0° C., and quenched with water (100 mL). The suspension was stirred for 30 minutes at room temperature and filtered. The solid was suspended in 100 mL of water, and the mixture was heated at 110° C. for 1 hour. The hot suspension was filtered and dried to obtain the title compound (1.10 g, 60% over 2 steps, HPLC purity 91.4%).

Example 29: Preparation of benzyl 4-amino-6-bromo-3-chloro-5-fluoropicolinate (Formula A2)

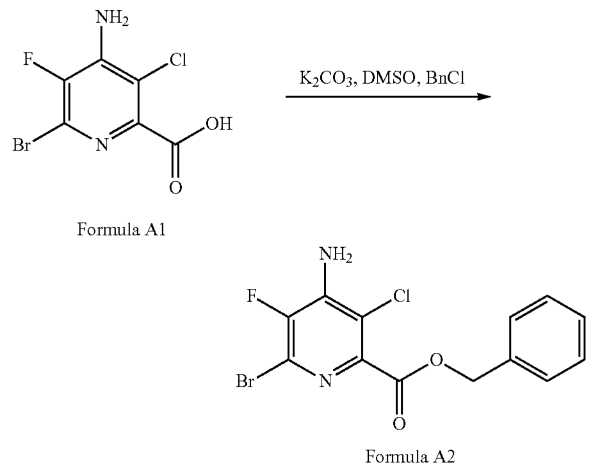

Formula A1

Formula A2

A 125 mL three-neck flask equipped with a magnetic stirrer, a cold water condenser, a thermocouple and a nitrogen pad was charged with 4-amino-6-bromo-3-chloro-5-fluoropicolinic acid (Formula A1; 5.0 g, 18.6 mmol) and DMSO (20 mL). The mixture was stirred, and powdered $K_2CO_3$ (2.82 g, 20.4 mmol) was added in portions over 10 minutes. A mild exotherm was observed with the temperature rising from 20 to 22.5° C. The mixture was stirred at ambient temperature for 30 minutes, and benzyl chloride (2.59 g, 20.4 mmol) was added in one portion. The resulting mixture was stirred at ambient temperature for 15 minutes, 40° C. for 5 hours, and 50° C. for 2 hours. The reaction mixture was cooled to ambient temperature, water (75 mL) was added, and the resulting mixture was stirred for 30 minutes. The solid was filtered, rinsed with water (20 mL), suction-dried and dried in vacuum oven at 50° C. overnight. The title compound was isolated (6.5 g, 97%): $^1H$ NMR (500 HMz, $CDCl_3$) δ 7.44 (m, 2H), 7.35 (m, 3H), 5.40 (s, 2H), 4.98 (br s, 2H); $^{19}F$ NMR δ −129.16.

Example 30: Preparation of benzyl 4-amino-6-bromo-3-chloro-5-fluoropicolinate (Formula A2)

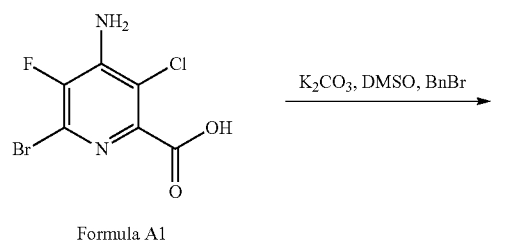

Formula A1

-continued

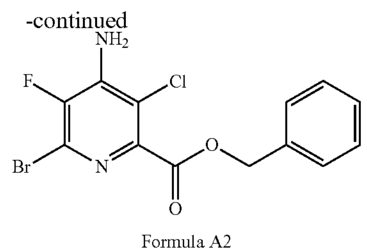

Formula A2

A sample of 4-amino-6-bromo-3-chloro-5-fluoropicolinic acid (Formula A1; 12.9 g, 82 wt % purity as estimated by $^1H$ NMR, 39.17 mmol, containing 18 wt % (13.94 mmol) of phthalic acid) was dissolved in DMSO (100 mL) in a 250 mL three-neck flask equipped with a magnetic stirrer, a cold water condenser, a thermocouple and a nitrogen pad. Powdered $K_2CO_3$ (9.95 g, 72 mmol) was added in portions over 10 minutes, resulting in a mild exothermic reaction with the temperature rising from 20 to 25° C. The mixture was stirred at ambient temperature for 30 minutes, and benzyl bromide (8.00 g, 46.8 mmol) was added slowly over 10 minutes while the temperature was maintained below 25° C. with a cold water bath. The resulting mixture was stirred at ambient temperature for 4 hours and was poured into cold water (300 mL). The resulting slurry was stirred for 15 minutes and was filtered. The solid was rinsed with water (100 mL), dried via suction, and washed with hexane (100 mL). Further drying at 45° C. in a vacuum oven overnight provide the title compound (13.4 g, 95%).

Example 31: Preparation of benzyl 4-amino-6-bromo-3-chloro-5-fluoropicolinate (Formula A2)

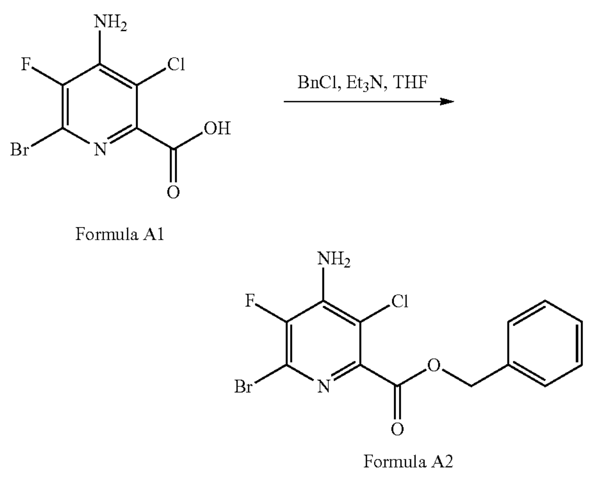

Formula A1

Formula A2

A sample of 4-amino-6-bromo-3-chloro-5-fluoropicolinic acid (Formula A1; 13.5 g, 47.6 mmol) was added to a 250 mL jacket reactor equipped with overhead agitation, a cold water condenser, a thermocouple and a nitrogen pad. THE (50 mL) was added giving a thin slurry. Triethylamine (7.1 g, 70.1 mmol) was added slowly. Benzyl chloride (8.9 g, 70.1 mmol) was added in one portion to the reaction mixture. The resulting mixture was heated to 65° C. and stirred for 18 hours. Liquid chromatographic analysis indicated >99% conversion. Additional triethylamine (0.3 equivalents) was added. The reaction mixture was cooled to room temperature after 16 hours. Brine (15 wt %, 20 g) was added to the mixture. The aqueous phase was discarded.

Example 32: Preparation of benzyl 4-amino-6-bromo-3-chloro-5-fluoropicolinate (Formula A2)

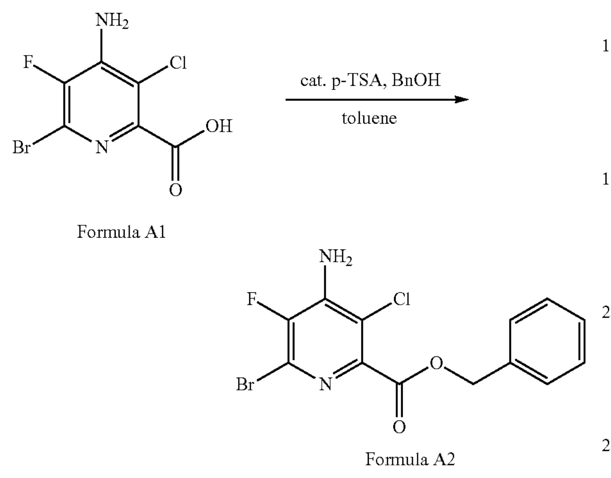

Formula A1

Formula A2

To a three-neck flask equipped with a stir bar, a heating mantle, and a Dean-Stark trap with condenser were added 4-amino-6-bromo-3-chloro-5-fluoropicolinic acid (Formula A1; 3.00 g, 11.1 mmol), benzyl alcohol (11.5 g), toluene, and p-toluenesulfonic acid monohydrate (p-TSA, 212 mg). The mixture was heated at 80° C. and slowly placed under a vacuum of 30 mm Hg in order to remove water that was generated in situ. After heating at 80° C. for 10 hours, the reaction mixture was cooled to ambient temperature. Cyclohexane (50 mL) was added dropwise, and the resulting slurry was stirred for 2 hours, cooled to 10° C., and filtered. The wet cake was rinsed with cyclohexane (10 mL) and water (20 mL), suction dried, rinsed with cyclohexane (5 mL), and dried at 45° C. under reduced pressure in a vacuum oven to provide the title compound (3.29 g, 82.3%).

Example 33: Comparative Preparations of

A. Benzyl 4-amino-3-chloro-6-(4-chloro-2-fluoro-3-methoxyphenyl)-5-fluoropicolinate (Formula I-A) from Formula A2 (a 6-bromopyridine Compound)

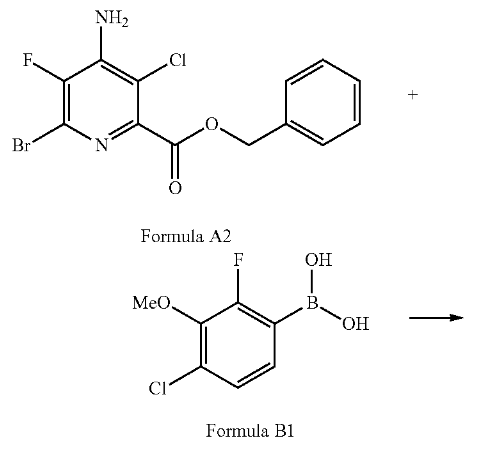

Formula A2

+

Formula B1

-continued

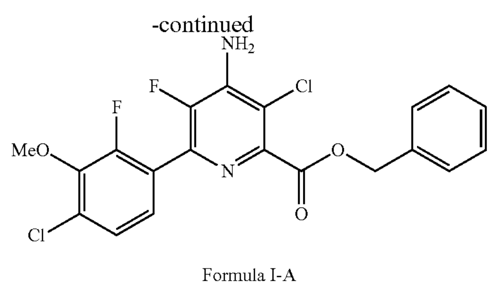

Formula I-A

A 50-mL three-neck flask equipped with a stir bar, a condenser, a thermocouple, and a nitrogen pad, was charged with benzyl 4-amino-6-bromo-3-chloro-5-fluoropicolinate (Formula A2; 1.80 g, 5.0 mmol), (4-chloro-2-fluoro-3-methoxyphenyl)boronic acid (B1; 1.12 g, 5.5 mmol), solid potassium bicarbonate ($KHCO_3$; 1.00 g, 10 mmol), THE (15 mL), and water (5 mL). The mixture was stirred and sparged with nitrogen gas for 30 minutes. Triphenylphosphine ($Ph_3P$; 26.2 mg, 0.1 mmol), and palladium acetate ($Pd(OAc)_2$; 11.2 mg, 0.050 mmol) were added under nitrogen. The mixture was heated and stirred at 60° C. for 16 hours. HPLC analysis of the reaction mixture showed the reaction gave 95.6 area % of the title compound, with only 3.0 area % of unreacted Formula C2, and no boronic acid.

B. Benzyl 4-amino-3-chloro-6-(4-chloro-2-fluoro-3-methoxyphenyl)-5-fluoropicolinate (Formula I-A) from 14 (a 6-chloropyridine Compound)

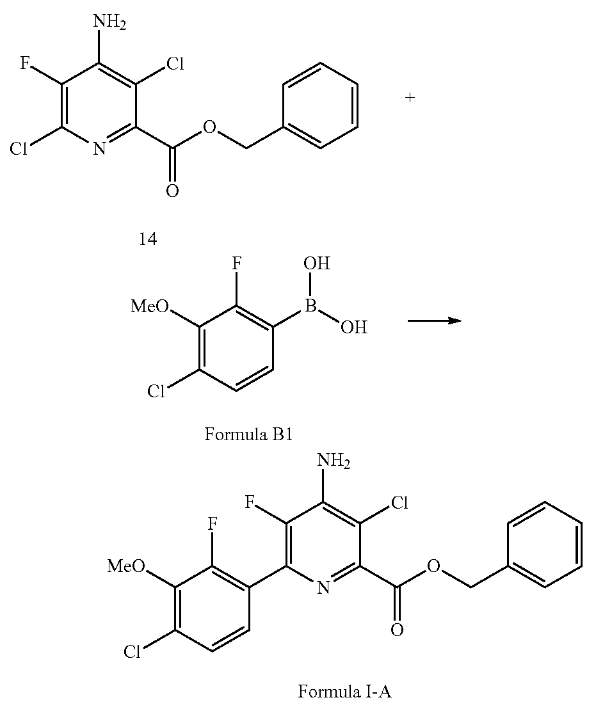

14

+

Formula B1

Formula I-A

A 50-mL three-neck flask equipped with a stir bar, a condenser, a thermocouple, and a nitrogen pad, was charged with benzyl 4-amino-3,6-dichloro-5-fluoropicolinate (Formula A1; 1.56 g, 5.0 mmol), (4-chloro-2-fluoro-3-methoxyphenyl)boronic acid (Formula B1; 1.12 g, 5.5 mmol), solid $KHCO_3$ (1.00 g, 10 mmol), THE (15 mL), and water (5 mL).

The mixture was stirred and sparged with nitrogen gas for 30 minutes. Triphenylphosphine ($Ph_3P$; 26.2 mg, 0.1 mmol), and palladium acetate ($(Pd(OAc)_2$; 11.2 mg, 0.050 mmol) were added under nitrogen. The mixture was heated and stirred at 60° C. for 16 hours. HPLC analysis of the reaction mixture showed the reaction gave 73.0 area % of the title compound, with only 22.9 area % of unreacted Formula A1, and no boronic acid (which means that the reaction stalled).

Example 34: Preparation of benzyl 4-amino-3-chloro-6-(4-chloro-2-fluoro-3-methoxyphenyl)-5-fluoropicolinate (Formula I-A)

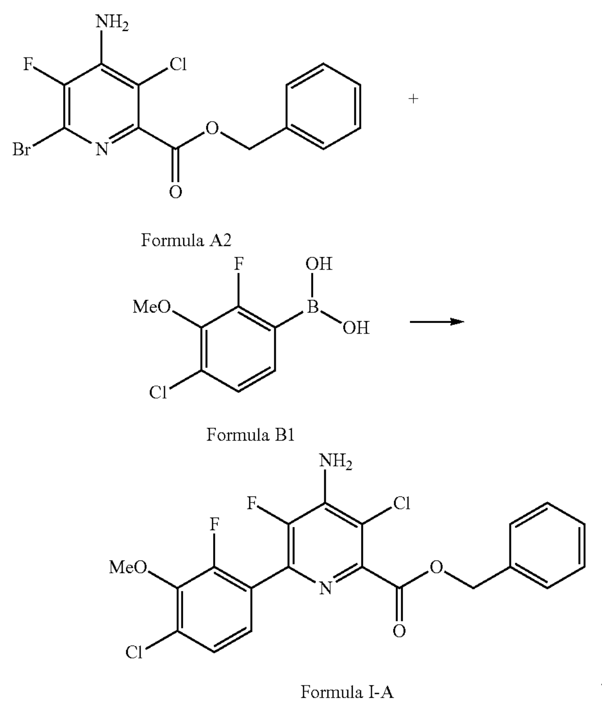

Formula A2

Formula B1

Formula I-A

A 1-L four-neck jacketed reactor equipped with an overhead agitator, distillation apparatus, a thermocouple, a nitrogen pad, was charged with benzyl 4-amino-6-bromo-3-chloro-5-fluoropicolinate (Formula A2; 30.0 g, 83.0 mmol), (4-chloro-2-fluoro-3-methoxyphenyl)boronic acid (Formula B1; 18.8 g, 92 mmol), potassium bicarbonate (18.7 g, 187 mmol), THF (250 mL) and water (83 mL). The mixture was stirred at 400 RPM and sparged with nitrogen gas for 30 minutes. Triphenylphosphine (438 mg, 1.67 mmol), and palladium acetate (186 mg, 0.83 mmol) were added. The mixture was heated to 60° C. for 5 hours. A sample was analyzed by HPLC, which showed 91 area % of the title compound, 7.4 area % of unreacted Formula A2. Additional (4-chloro-2-fluoro-3-methoxyphenyl)boronic acid (1.90 g, ~0.10 eq) was added, and the reaction mixture was stirred until Formula A2 was consumed. The reaction mixture was cooled to ambient temperature. The two phases were separated. The aqueous phase was extracted with THE (50 mL). The organic phases were combined. After removal of residual palladium compounds from the combined organic phase, the organic phase was concentrated to about 100 mL. Water (300 mL) was added with stirring to form a suspension. The suspension was filtered. The wet cake was rinsed with water (100 mL) and dried to give the title compound (36.0 g; 89%).

The compositions and methods of the claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

What is claimed is:

1. A process for the preparation of a 6-aryl-4-aminopicolinate of Formula I-A:

Formula I-A

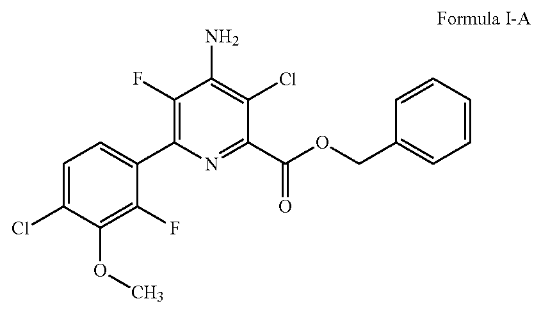 [SMILES: COc1c(Cl)ccc(-c2nc(C(=O)OCc3ccccc3)c(Cl)c(N)c2F)c1F]

the process comprising the following steps:

a. creating a first mixture containing a compound of Formula C2

Formula C2

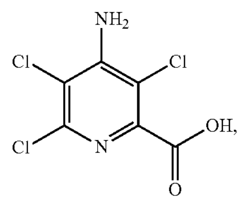

an acid, wherein the acid is concentrated sulfuric acid, or an acid-chloride forming compound, wherein the acid-chloride-forming compound is selected from the group consisting of thionyl chloride and oxalyl chloride, and an alcohol ROH, wherein R represents $C_1$-$C_{12}$ alkyl;

b. heating the first mixture at a temperature from about 70° C. to about 90° C.;

c. isolating from the first mixture the compound of Formula D2

Formula D2

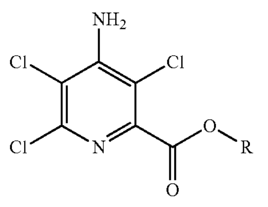

wherein

R represents $C_1$-$C_{12}$ alkyl;

d. creating a second mixture containing the compound of Formula D2;

phthalic anhydride

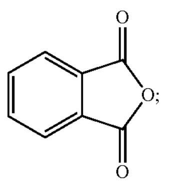 [SMILES: O=C1OC(=O)c2ccccc21]

a base selected from the group consisting of trimethylamine, triethylamine, tripropylamine, pyridine, 2-picoline, and 3-picoline; and a solvent selected from the group consisting of acetonitrile, toluene, N,N-dimethylformamide (DMF), propionitrile, benzonitrile, tetrahydrofuran (THF), 2-methyl-THF, dioxane, cyclopentyl methyl ether (CPME), monoethyleneglycol ethers, diethyleneglycol ethers, monopropyleneglycol ethers, dipropyleneglycol ethers, and methyl isobutyl ketone (MIBK), and mixtures thereof;

e. heating the second mixture at a temperature from about 25° C. to about 100° C.;

f. isolating from the second mixture the compound of Formula E2 wherein

Formula E2

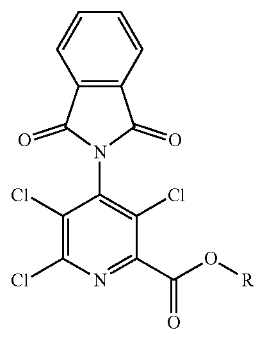

R represents $C_1$-$C_{12}$ alkyl;

g. creating a third mixture containing the compound of Formula E2; a fluorinating compound selected from the group consisting of potassium fluoride (KF), cesium fluoride (CsF), tetramethylammonium fluoride (TMAF), and mixtures thereof, or a mixture of tetramethylammonium chloride (TMAC) with KF or CsF; and a solvent selected from the group consisting of acetonitrile, propionitrile, benzonitrile, dimethylsulfoxide (DMSO), N,N'-dimethylformamide (DMF), sulfolane, N,N-dimethylacetamide (DMA), 1,1-dimethyl-2-imidazolidinone (DMI), N,N'-dimethylpropyleneurea (DMPU), N-methylpyrrolidinone (NMP), tetrahydrofuran (THF), 2-methyltetrahydrofuran (2-methyl-THF), dioxane, monoethyleneglycol ethers, diethyleneglycol ethers, monopropyleneglycol ethers, dipropyleneglycol ethers, and mixtures thereof;

h. heating the third mixture at a temperature from about 25° C. to about 110° C.;

i. isolating from the third mixture a compound of Formula F2

Formula F2

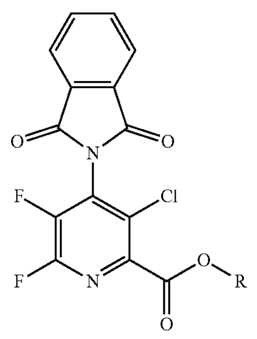

wherein

R represents $C_1$-$C_{12}$ alkyl;

j. creating a fourth mixture containing the compound of Formula F2;

hydrobromic acid (HBr); acetic acid; and water;

k. heating the fourth mixture at a temperature from about 50° C. to about 110° C.;

l. isolating from the fourth mixture the compound of Formula A1 or the hydrobromide (HBr) salt thereof Formula A1

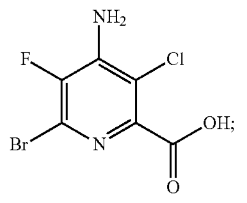

m. creating a fifth mixture containing the compound of Formula A1; and arylalkyl halide $RX^1$, a base selected from the group consisting of triethylamine, N,N-diisopropylethylamine, 3,5-lutidine, 2,6-lutidine, 3-methylpyridine, lithium carbonate, and potassium carbonate, and a solvent selected from the group consisting of tetrahydrofuran, dimethyl sulfoxide, N,N-dimethylformamide, dichloromethane, and 1,2-dichloroethane wherein R represents $C_6$-$C_{12}$ arylalkyl; and $X^1$ represents Cl or Br;

n. heating the fifth mixture at a temperature from about 25° C. to about 80° C. to form a sixth mixture;

o. adding to the sixth mixture a compound of Formula B1

Formula B1

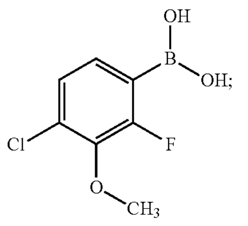

one or more bases selected from the group consisting of potassium carbonate, potassium bicarbonate, sodium carbonate, sodium bicarbonate, potassium acetate, sodium acetate, potassium phosphate monobasic, potassium phosphate dibasic, potassium phosphate tribasic, sodium tetraborate, potassium hydroxide, sodium hydroxide, triethylamine, triisopropylamine, diisopropylamine, diethylamine, and diisopropylethylamine; one or more solvents selected from the group consisting of methyl isobutyl ketone (MIBK), dimethoxyethane (DME), tetrahydrofuran (THF), methanol (MeOH), benzyl alcohol, toluene, water, and mixtures thereof; a palladium catalyst selected from the group consisting of palladium (II) acetate ($Pd(OAc)_2$) and palladium (II) chloride ($PdCl_2$); and optionally a ligand selected from the group consisting of tri-tert-butylphosphine, tricyclohexylphosphine, di-tert-butylphenylphosphine, dicyclohexylphenylphosphine, triphenylphosphine, 4-diphenylphosphinomethyl polystyrene resin cross-linked, sodium diphenylphosphinobenzene-3-sulfonate with 2% DVB, tri (p-tolyl)phosphine, and (±)-2,2'-bis(diphenylphosphino)-1,1'-binaphthyl;

p. heating the sixth mixture to a temperature of between about 25° C. and about 100° C.; and q. isolating the 6-aryl-4-aminopicolinate of Formula I-A from the sixth mixture.

* * * * *